United States Patent
Hayes et al.

(10) Patent No.: US 11,086,073 B2
(45) Date of Patent: Aug. 10, 2021

(54) GUIDEWIRE HAVING A FIBER OPTIC FORCE SENSOR WITH A MIRROR HAVING A PATTERNED REFLECTANCE

(71) Applicant: Lake Region Manufacturing, Inc., Chaska, MN (US)

(72) Inventors: John Michael Hayes, Cork (IE); Jim Kelley, Coon Rapids, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 17/144,447

(22) Filed: Jan. 8, 2021

(65) Prior Publication Data

US 2021/0215871 A1 Jul. 15, 2021

Related U.S. Application Data

(60) Provisional application No. 62/959,234, filed on Jan. 10, 2020.

(51) Int. Cl.
*G02B 6/02* (2006.01)
*G01L 1/24* (2006.01)
(Continued)

(52) U.S. Cl.
CPC ......... *G02B 6/02042* (2013.01); *G01D 5/268* (2013.01); *G01L 1/242* (2013.01);
(Continued)

(58) Field of Classification Search
CPC ............ G02B 6/02042; G02B 6/02004; G02B 6/4415; G02B 6/241; G01L 1/242; G01D 5/268
See application file for complete search history.

(56) References Cited

U.S. PATENT DOCUMENTS

| | | | |
|---|---|---|---|
| 6,868,736 B2 * | 3/2005 | Sawatari | G01L 9/0042 73/800 |
| 2008/0009750 A1 | 1/2008 | Aeby et al. | |

(Continued)

FOREIGN PATENT DOCUMENTS

WO 2012029013 A1 3/2012

OTHER PUBLICATIONS

"European Search Report, Application No. 21151011.0 dated Jun. 1, 2021".

(Continued)

*Primary Examiner* — John Bedtelyon
(74) *Attorney, Agent, or Firm* — Michael F. Scalise

(57) ABSTRACT

A guidewire having a fiber optic force sensor with a mirror having encoded reflectance is described. The guidewire has a distal housing supported by a core wire. A distal hypotube connected to the distal housing supports a spring intermediate hypotube proximal and distal portions. An atraumatic head is connected to the distal hypotube portion. An optical fiber having at least one fiber core extends through lumens in the core wire and housing to a distal end of the housing. A mirror supported by the atraumatic head faces proximally but is spaced distally from the fiber core at a distal face of the optical fiber. The mirror is provided with a pattern of reflectance that varies along a radius from a central area of reflectance. Light of a defined power shines from the fiber core to the mirror with a reflected percentage of the defined light power being reflected back to the fiber core. A percentage of the reflected percentage of the defined light power is captured by and travels along the fiber core to a light wave detector connected to a controller. From the percentage of the reflected percentage of the light of the defined power received by the detector, the controller is programmed to calculate whether an axial or lateral force is (Continued)

imparted to the atraumatic head and, if so, the magnitude and vector of those forces.

27 Claims, 14 Drawing Sheets

(51) Int. Cl.
  *G01D 5/26* (2006.01)
  *G02B 6/44* (2006.01)
  *G02B 6/24* (2006.01)
(52) U.S. Cl.
  CPC ....... *G02B 6/02004* (2013.01); *G02B 6/4415* (2013.01); *G02B 6/241* (2013.01)

(56) References Cited

U.S. PATENT DOCUMENTS

| | | | |
|---|---|---|---|
| 2009/0177095 A1 | 7/2009 | Aeby et al. | |
| 2016/0273988 A1* | 9/2016 | Zhou | G01H 9/004 |
| 2017/0181646 A1* | 6/2017 | Hayes | A61B 5/0215 |

OTHER PUBLICATIONS

Peirs, "A micro optical force sensor for force feedback during minimally invasive robotic surgery".

\* cited by examiner

US 11,086,073 B2

GUIDEWIRE HAVING A FIBER OPTIC FORCE SENSOR WITH A MIRROR HAVING A PATTERNED REFLECTANCE

CROSS-REFERENCE TO RELATED APPLICATION

This application claims priority to U.S. Provisional Application Ser. No. 62/959,234, filed on Jan. 10, 2020.

BACKGROUND OF THE INVENTION

1. Field of the Invention

The present invention relates to the field of medical devices, and specifically to a guidewire for treating a medical condition in a patient. An exemplary medical condition is the treatment of an occlusion attributed to atherosclerosis.

2. Prior Art

Atherosclerosis is the narrowing or occlusion of an artery due to a build-up of plaque and is the most common cause of cardiovascular disease. Occlusions result in impaired blood flow in an artery, which can cause angina, heart attack, heart failure, limb impairment, or limb loss.

To diagnose and treat arteriosclerosis, a guidewire is inserted into the vascular system of a patient through an accessible artery such as the femoral artery. Then, the guidewire is moved through the vasculature to the occluded vessel area. Navigation of the guidewire can be achieved by rotating its external proximal end while pushing forward. The position of a conventional guidewire is typically visualized by 2D x-ray imaging with contrast fluid. Diagnostic and treatment catheters are then delivered over the guidewire to the diseased area.

While 2D x-ray imaging is an acceptable means for visualizing the progress of a guidewire through the vasculature, there is a desire to improve the real-time positional accuracy of the guidewire in the vasculature during a medical procedure. Moreover, during forward steering of the guidewire, frictional feedback from the surface of the shaft of the guidewire dominates the tactile feel in the surgeon's hand while tactile perception of the force acting at the atraumatic head of the guidewire is minimal. The lack of tactile perception at the atraumatic head presents a risk of vessel injury such as perforation due to the force of the guidewire atraumatic head against vasculature tissue.

SUMMARY OF THE INVENTION

To overcome the shortcomings of conventional methods for tracking the path of a guidewire through the vasculature, a guidewire according to the present invention has a core wire extending along a longitudinal axis from a core wire proximal end to a core wire distal portion having a core wire distal end. A core wire lumen extends to the core wire proximal and distal ends. A housing supported by the core wire distal portion has a housing lumen in open communication with the core wire lumen. A hypotube providing a hypotube lumen extends from a hypotube proximal portion to a hypotube distal portion. A spring is supported by the hypotube intermediate its proximal and distal portions. An atraumatic head is connected to the hypotube distal portion. An optical fiber extending through the core wire and housing lumens to the housing distal end has at least one fiber core. A mirror supported by the atraumatic head faces proximally but is spaced distally from the fiber core at the distal face of the optical fiber. The reflectivity of the mirror varies across its surface.

In use, the optical fiber is optically connected to a light source and a light power detector. Light of a defined power emitted by the light source into the fiber core shines on the mirror and a percentage of the defined light power (a reflected light percentage) is reflected toward the fiber core. Then, a percentage of the reflected light percentage is captured by and travels down the fiber core to the light power detector connected to a controller. In other words, a percentage of the light power emitted by the light source into the fiber core is reflected by the mirror toward the distal face of the optical fiber. Then, a lesser percentage of the reflected light percentage is captured by (a captured light percentage) and travels back down the fiber core to the light power detector. The detector is configured to determine the intensity or power in the reflected and captured light with respect to the defined power of the light emitted by the light source into the fiber core. The reflected and captured light received by the light power detector has a somewhat lesser power than the originally emitted light. The controller is programmed to determine the difference between the power of the originally emitted light and that of the reflected and captured light received by the detector and to convert that difference into a force imparted to the atraumatic head in the vasculature.

For example, in a neutral orientation without any axial or lateral forces imparted to the atraumatic head, the atraumatic head is aligned along the longitudinal axis of the core wire of the guidewire with the mirror spaced a first distance from the distal face of the optical fiber. Then, with only an axial force but no lateral force imparted to the atraumatic head, the atraumatic head is still axially aligned with the core wire, but now the mirror is at a second, lesser distance from the distal face of the optical fiber. Since the mirror is closer to the distal face of the optical fiber, the diminution in power of the reflected and captured light that travels back down the fiber core to the light power detector is less than with the mirror at the first, greater distance from the optical fiber. The controller connected to the light power detector is programmed to convert the difference in reflected and captured light power with the mirror spaced at the first and second distances from the fiber core of the optical fiber into a magnitude of the axial force imparted to the atraumatic head.

When calculating for both axial and lateral forces, it is known in the prior art to have three fiber cores extending through the optical fiber. With the atraumatic head of the guidewire tilted both axially and laterally out of alignment with respect to the neutral position without any imparted force, the three fiber cores each receive reflected light having a different power. Respective light detectors detect the power of the reflected and captured light traveling through the fiber cores and transmit this power information to the controller. The controller in turn calculates the position of the atraumatic head in an x, y, z coordinate system through the differences in the reflected and captured light power received by each of the three fiber cores. This is commonly known as triangulation.

However, according to the present invention, the mirror is provided with a patterned reflectance that varies along a radius from a central area of reflectance. The patterned reflectance of the mirror means that triangulation can be performed with greater accuracy and that the position of the atraumatic head in an x, y, z coordinate system can be determined with the optical fiber having a single fiber core. A single fiber core does not normally lend itself to triangulation.

In one embodiment of the present guidewire, the patterned reflectance of the mirror comprises a central area of reflectance having a first light reflectance $R_1$ and at least one annular ring of reflectance having a second light reflectance $R_2$. Reflectance $R_1$ is different than reflectance $R_2$.

In the case without any axial or lateral force imparted to the atraumatic head, first percentages of the defined light power from the light reflectances $R_1$ and $R_2$ are reflected toward the fiber core at the distal face of the optical fiber. Then, second, lesser percentages of the first percentages are captured by and travel down the fiber core to the light power detector connected to the controller. The first percentages are less than the defined light power that was initially emitted into the fiber core by the light source and the second percentages are less than the first percentages.

In the situation with only an axial force imparted to the atraumatic head, the atraumatic head is still axially aligned with the core wire, but the mirror is spaced a second distance from the distal face of the optical fiber. The second distance is less than the first distance. In this orientation, axial force dependent reflected and captured percentages of the defined light power from the mirror reflectances $R_1$ and $R_2$ are received by the controller via the fiber core. The controller then calculates the magnitude of the axial force imparted to the atraumatic head by comparing reflected and captured percentages of light power from the light reflectances $R_1$ and $R_2$ without any axial force to the reflected and captured light power from the light reflectances $R_1$ and $R_2$ to determine the distance the atraumatic head has moved along the longitudinal axis, and hence the magnitude of the axial force imparted to the atraumatic head.

The magnitude of the axial force is based on Hooke's law which states that the force (F) needed to extend or compress a spring by some distance (x) scales linearly with respect to that distance. That is, $F_s=kx$, where k is a constant factor characteristic of the spring (i.e., its stiffness), and x is small compared to the total possible deformation of the spring.

Further, in the situation where both axial and lateral forces are imparted to the atraumatic head, the atraumatic head deflects out of axial and lateral alignment with respect to the core wire and the distal face of the optical fiber. The mirror is now spaced a third distance from the fiber core, the third distance being different than the first and second distances. In comparison to the reflected and captured light power percentages of the defined light power from the light reflectances $R_1$ and $R_2$ without any axial force or with only an axial force, axial and lateral force induced reflected light power percentages of the defined light power reflect toward the distal face of the optical fiber with a lesser percentage of the reflected light power captured by and traveling along the fiber core to the light power detector. The controller calculates the magnitude and vector of the axial and lateral forces imparted to the atraumatic head from the reflected and captured light power percentages of the defined light power from the light reflectances $R_1$ and $R_2$ in comparison to those percentages without any axial force or with only an axial force imparted to the atraumatic head. It is the mirror having at least the two light reflectances $R_1$ and $R_2$ that enables the controller to determine the magnitude of the axial and lateral forces imparted to the atraumatic head of the guidewire.

In addition to determining the amount of force that the atraumatic head is exerting against body tissue, the controller is programmed to use the axial and lateral forces imparted to the atraumatic head to determine an exact orientational value in an x, y, z coordinate system of the atraumatic head out of axial alignment with the guidewire body. The controller is programmed to present the orientational and force data in real-time on a visual display.

If desired, the mirror has a patterned reflectance comprising the central area of reflectance having the first light reflectance $R_1$ and at least first, second, and third annular rings of reflectance having respective second, third and fourth light reflectances $R_2$, $R_3$ and $R_4$ at progressively greater first, second and third radial distances from the central area of reflectance; the light reflectances $R_1$, $R_2$, $R_3$ and $R_4$ being different from each other.

In a further embodiment of a guidewire according to the present invention, the patterned reflectance comprising the central area of reflectance $R_1$ and the second, third and fourth light reflectances $R_2$, $R_3$ and $R_4$ of the respective first, second and third annular rings of reflectance are each divided into quadrants of reflectance; the quadrants of reflectance of each of the light reflectances $R_1$, $R_2$, $R_3$ and $R_4$ being different from each other.

Moreover, in another embodiment of a guidewire according to the present invention, the patterned reflectance comprising the central area of reflectance $R_1$ and the second, third and fourth light reflectances $R_2$, $R_3$ and $R_4$ of the respective first, second and third annular rings of reflectance are each divided into fractional segments of reflectance; the fractional segments of reflectance of each of the light reflectances $R_1$, $R_2$, $R_3$ and $R_4$ being different from each other.

If desired, the controller also uses the force data at the atraumatic head to generate an input signal to an electromechanical vibrator integrated into the guidewire's optical connector so that the surgeon receives force feedback at the hand. This increased feedback to the surgeon helps reduce the risk of damaging vasculature tissue, speeds up medical procedures and reduces contrast fluid and x-ray use. Also, the force data correlates with the hardness of tissue encountered by the guidewire so that the occlusion orientation can be determined precisely, thereby reducing the x-ray requirement further. The force data at the occlusion also gives information to the surgeon regarding the makeup of the blockage such as how calcified it is. This type of information is useful in helping the surgeon make treatment decisions such as whether to insert a stent, or not.

After the force imparted to the atraumatic head and the orientation of the guidewire in the vasculature is ascertained, the optical connector enables the proximal and distal optical fibers to be disconnected from each other. Then, a diagnostic or therapeutic instrument, for example a catheter, can be moved along the guidewire to the point of interest in the vasculature of the patient. If the guidewire is left in the vasculature during the medical procedure, the optical connector enables the guidewire and its distal optical fiber to be optically re-connected to the proximal optical fiber. This is useful for letting the surgeon continue to monitor the orientation of the guidewire during the medical procedure. Also, the guidewire needs to be able to be inserted at any rotational angle without significant power loss between the distal and proximal optical fibers across the optical connector.

These and other aspects of the present invention will become increasingly more apparent to those skilled in the art by reference to the following detailed description and to the appended drawings.

DETAILED DESCRIPTION OF THE PREFERRED EMBODIMENTS

Figure 1:
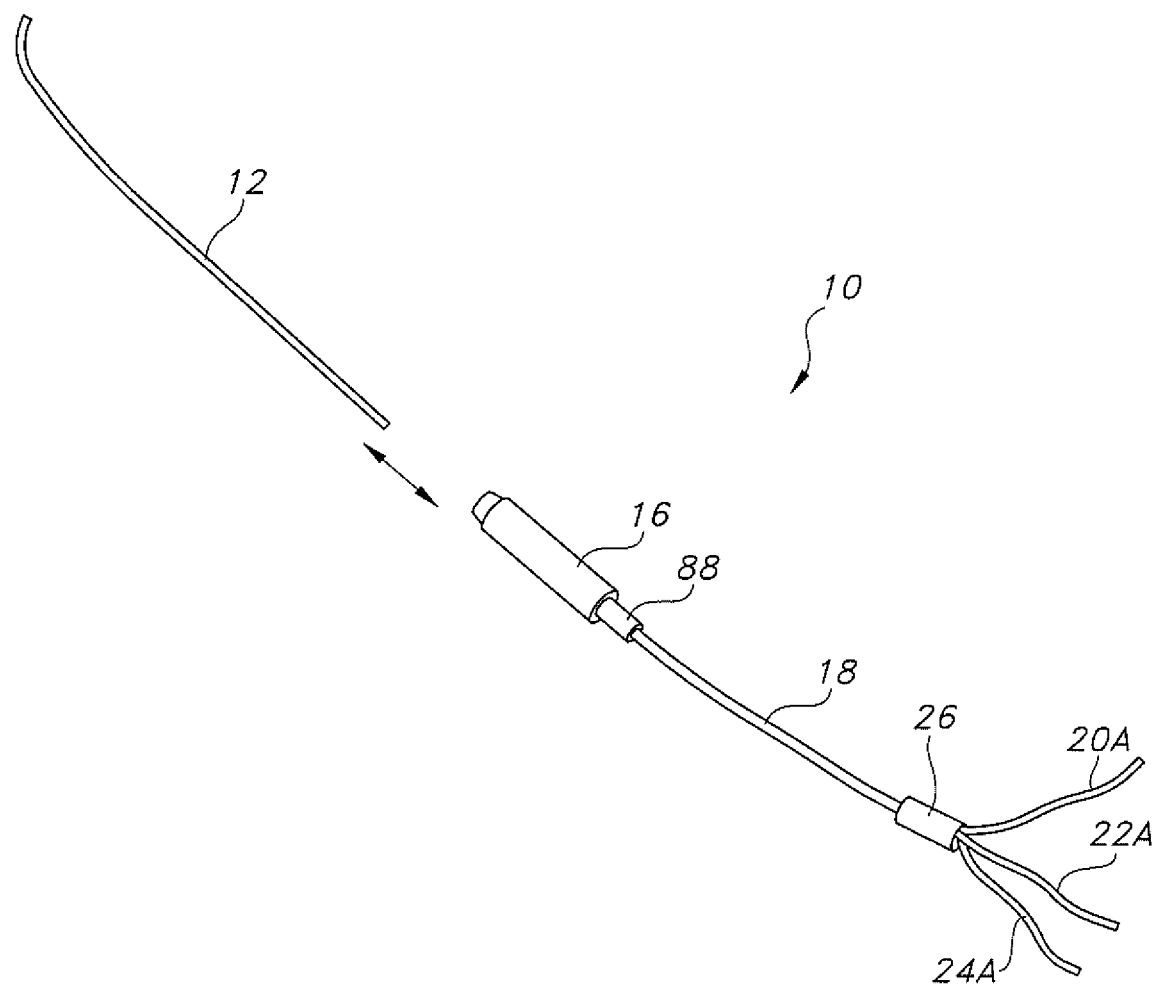
FIG. 1 is a schematic view of a guidewire system 10 according to the present invention.

Turning now to the drawings, FIG. 1 is a schematic of a guidewire system 10 according to the present invention. The guidewire system 10 comprises a guidewire 12 supporting an optical fiber 14 (FIGS. 2, 2A, 2B, 3 to 7, 9, 9A, 9B, 12, 12A, 12B and 13). The guidewire and optical fiber are detachably connectable to an optical connector 16 serving as a handle. An external optical cable 18 is connected to the optical connector 16 opposite the guidewire 12. The guidewire 12 has a length ranging from about 50 cm to about 350 cm.

Figure 2:
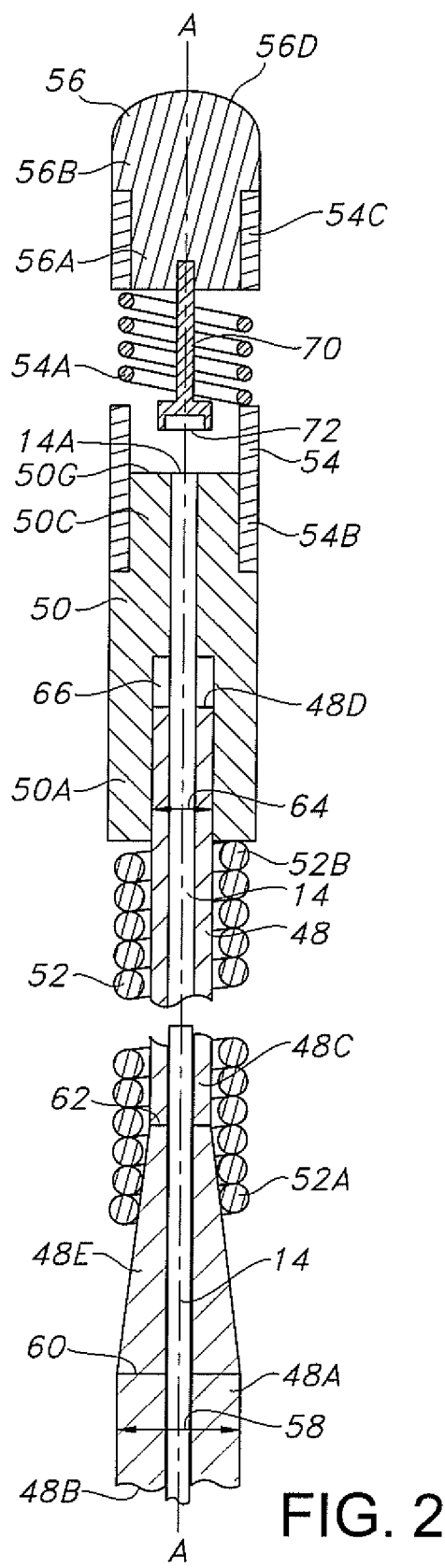
FIG. 2 is a partial cross-sectional view of the guidewire 12 shown in FIG. 1 including a core wire 48 supporting an optical fiber 14 and with the atraumatic head 56 supporting a mirror 72 facing proximally but distally spaced from a distal face of the optical fiber.
Figure 2C:
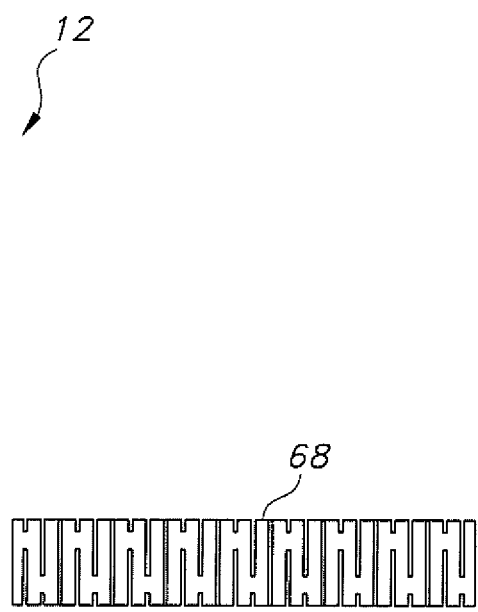
FIG. 2C shows that the spring of the distal hypotube 54/spring 54A subassembly shown in FIG. 2 is a slotted spring 55.
Figure 2A:
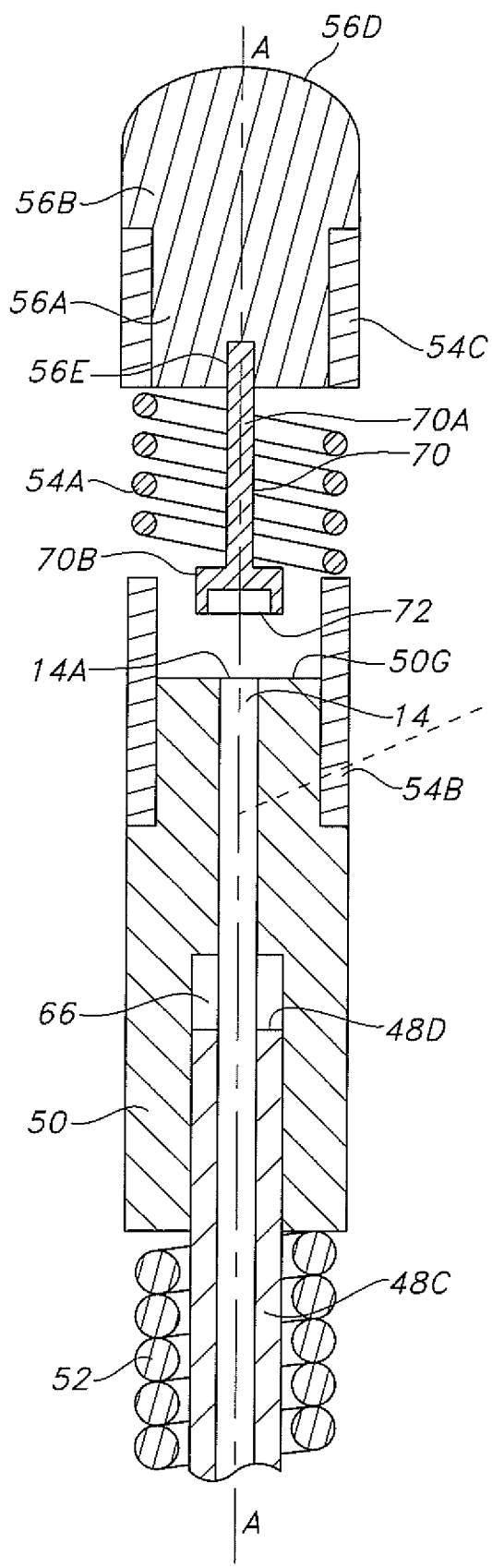
FIG. 2A is an enlarged, partial cross-sectional view of the distal portion of the guidewire 12 shown in FIG. 2.
Figure 2B:
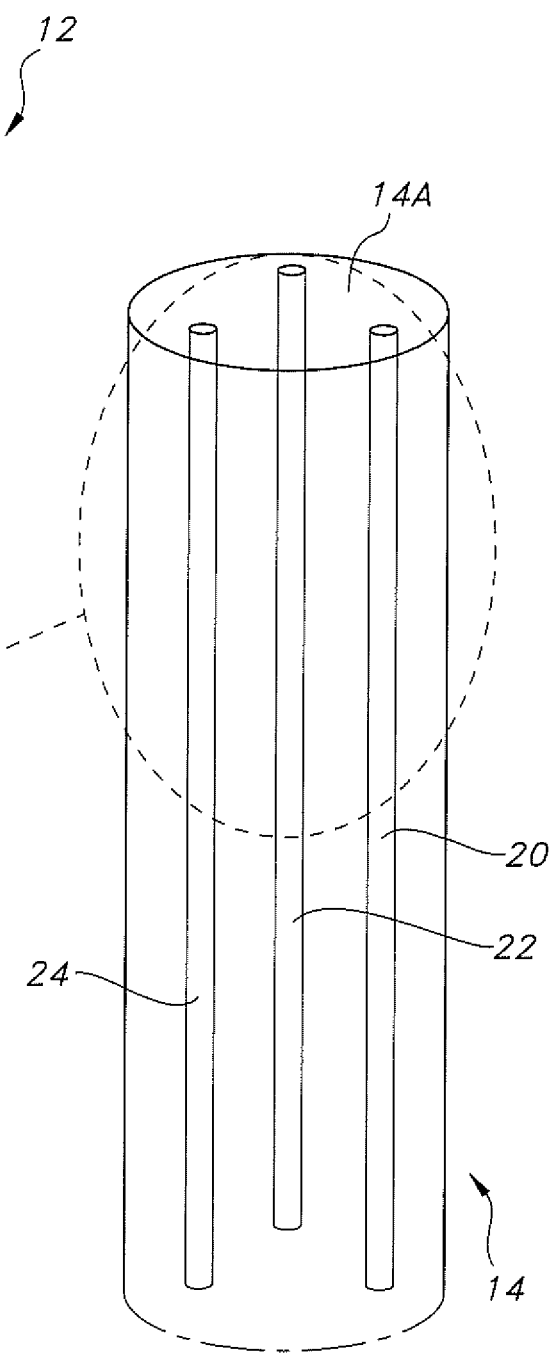
FIG. 2B is an enlarged view of the indicated region in FIG. 2A showing the optical fiber 14 supporting fiber cores 20, 22 and 24.

As will be described in detail hereinafter, in one embodiment the optical fiber 14 supported by the guidewire 12 has three fiber cores 20, 22 and 24 (FIG. 2B). The external optical cable 18 has an external optical fiber 18A (FIGS. 6 and 7) comprising three external fiber cores 20A, 22A and 24A (FIGS. 1 and 8) that are optically connected through the optical connector 16 to the respective fiber cores 20, 22 and 24 of the guidewire optical fiber 14. A proximal end of the optical cable 18 connects to a manifold 26 (FIG. 1) where the fiber cores 20A, 22A and 24A of the external optical fiber 18A fan out for connection to respective circulators 28, 30 and 32 which, in turn, are optically connected to respective broadband light sources 34, 36 and 38, and light power detectors 40, 42 and 44, all connected to a controller 46 (FIG. 8) serving as a computer.

FIG. 2 is a partial cross-sectional view of an exemplary embodiment of the guidewire 12 shown in FIG. 1. The guidewire 12 is comprised of a core wire 48 that extends along a longitudinal axis A-A and supports an intermediate housing 50 residing between a proximal coil spring 52 and a distal hypotube 54/spring 54A subassembly. An atraumatic head 56 is connected to the distal hypotube 54/spring 54A subassembly.

As particularly shown in FIG. 2, the core wire 48 extends from a cylindrically-shaped core wire proximal portion 48A having a proximal end 48B to a cylindrically-shaped core wire distal portion 48C having a distal end 48D. In this exemplary embodiment, the core wire 48 has a substantially constant first outer diameter 58 extending from the core wire proximal end 48B to a first transition indicated at 60. An exemplary first outer diameter ranges from about 0.004 inches to about 0.030 inches. A tapered portion 48E extends distally and downwardly towards the longitudinal axis A-A from the first transition 60 to a second transition indicated at 62 where the core wire distal portion 48C begins. The cylindrically-shaped distal portion 48C has a substantially constant second outer diameter 64, which is less than the first outer diameter 58. An exemplary second outer diameter is about 0.0075 inches. The distal portion 48C extends distally to the distal end 48D of the core wire.

If desired, the core wire 48 can be provided with more than one tapered portion. For example, there can be two or more tapered portions, each residing between proximal and distal cylindrically-shaped core wire portions. The core wire 48 is preferably made of stainless steel or nitinol. Nitinol is a superelastic nickel-titanium alloy wire comprising, for example, a composition in the range of from about 54 atomic % nickel: about 46 atomic % titanium to about 57 atomic % nickel: about 43 atomic % titanium.

The proximal coil spring 52 is made of stainless steel, preferably 304 stainless steel, and has a proximal end 52A connected to the tapered portion 48E of the core wire 48. The opposite distal end 52B of the proximal coil spring terminates at the intermediate housing 50, proximal the core wire distal end 48D. That way, the core wire distal portion 48C extends distally and axially outwardly beyond a distal end of the proximal coil spring 52. The connections between the proximal end of the proximal coil spring 52A and the tapered portion 48E of the core wire and between the distal end 52B of the proximal coil spring and the intermediate housing 50 are individually made as a laser welder, a braze, or using a solder, and the like.

Figure 3:
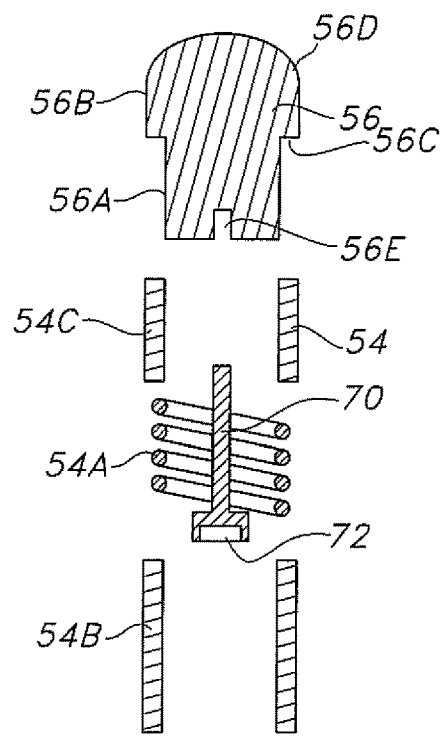
FIG. 3 is an exploded, partial cross-sectional view of the distal portion of the guidewire 12 shown in FIG. 2A.

FIGS. 2, 2A and 3 illustrate that the intermediate housing 50 supported on the cylindrically-shaped distal portion 48C of the core wire 48 has a cylindrically-shaped proximal portion 50A that extends distally to an outer annular step 50B (FIG. 3) meeting a cylindrically-shaped distal portion 50C. A proximal lumen 50D extends from a proximal end of the housing part-way along the length of the proximal portion 50A. The proximal lumen 50D of the housing meets a distal lumen 50E at an inner annular step 50F with the distal lumen 50E extending the rest of the length of the housing to a distal end thereof.

The distal portion 48C of the core wire 48 is received in the proximal lumen 50D of the housing 50, however, a gap 66 (FIG. 2) resides between the distal end 48D of the core wire and the inner step 50F. The gap 66 allows the optical fiber 14 to bend from the axially centered lumen of the housing 50 toward the outer surface of the core wire 48. Suitable materials for the intermediate housing 50 include stainless steel, nickel, titanium, platinum, platinum iridium, and a medical grade durable plastic.

The distal hypotube 54/spring 54A subassembly is a cylindrically-shaped member having the coil spring 54A residing between a proximal sleeve-shaped portion 54B and a distal sleeve-shaped portion 54C. Alternately, FIG. 2C shows that the spring of the distal hypotube 54/spring 54A subassembly is a slotted spring 68 residing between the proximal and distal sleeve-shaped portions 54B, 54C. Whether it is a coil spring 54A or a slotted spring 68, the distal spring is preferably made of stainless steel or nitinol.

The distal cylindrically-shaped portion 50C of the intermediate housing 50 is received inside the proximal sleeve 54B of the distal hypotube 54/spring 54A subassembly. In that manner, the outer surface of the intermediate housing 50 is substantially coaxially aligned with the outer surface of the distal hypotube 54/spring 54A subassembly.

In an alternate embodiment, intermediate housing 50 and the distal hypotube 54/spring 54A subassembly are a unitary or single member.

The atraumatic head 56 has a cylindrically-shaped proximal head portion 56A that extends to a distal head portion 56B of a greater diameter than the proximal head portion. The proximal and distal head portions 56A, 56B meet at an outer annular step 56C (FIG. 3). In turn, the cylindrically-shaped distal head portion 56B extends to a dome-shaped atraumatic surface 56D that is polished smooth to help minimize tissue damage and trauma as the guidewire 12 is moved through a vasculature. With the proximal portion 56A of the atraumatic head 56 received inside the lumen formed by the distal sleeve 54C of the distal hypotube 54/spring 54A subassembly, the cylindrically-shaped outer surface of the distal spring 54A is substantially coaxially aligned with the cylindrically-shaped outer surface of the distal portion 56B of the atraumatic head 56. Suitable materials for the atraumatic head 56 include stainless steel, nickel, titanium, platinum, and platinum/iridium.

The atraumatic head 56 is further provided with an inner blind bore 56E that is aligned along the longitudinal axis A-A of the core wire 48. The blind bore 56E terminates proximal the atraumatic surface 56D and receives the stem 70A of a mirror pedestal 70. The mirror pedestal 70 has a cup-shaped cradle 70B connected to the stem 70A. A highly polished mirror 72 is nested in the cradle 70B opposite the stem 70A. With the guidewire 12 in a neutral position without any axial or lateral forces imparted to the atraumatic head 56, the mirror 72 faces proximally, aligned along the longitudinal axis A-A.

Figure 4:
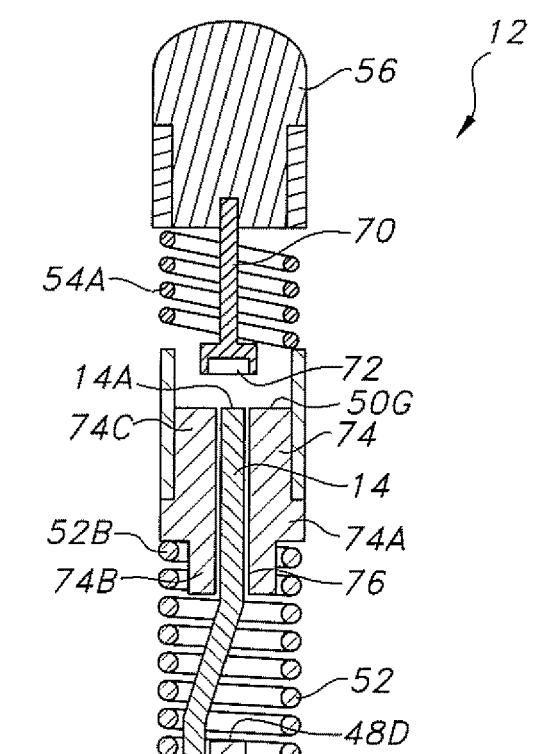
FIG. 4 is a cross-sectional view of the distal portion of the guidewire 12 shown in FIGS. 2 and 2A with the optical fiber 14 residing in a groove 78 in the core wire 48.

FIG. 4 illustrates an alternate embodiment of a guidewire 12A according to the present invention. Guidewire 12A has the core wire 48 terminating proximal an intermediate housing 74. The housing 74 has an enlarged intermediate cylindrically-shaped portion 74A located between proximal and distal cylindrically-shaped portions 76B, 74C. A lumen 76 extends through the housing to the opposed ends of the proximal and distal cylindrical portions 74B and 74C. The distal end of the coil spring 52 is secured to the housing 74 where the intermediate and proximal cylindrical portions 74A and 74B meet. Opposite the spring 52, the proximal sleeve-shaped portion 54B of the distal hypotube 54/spring 54A subassembly is secured to the distal cylindrical portion 74C of the housing 74. The distal end 48D of the core wire 48 is spaced proximally from the housing 74 with the coil spring 52 bridging this distance. This embodiment of the guidewire 12A is somewhat more flexible than the guidewire 12 shown in FIGS. 2, 2A and 3.

FIG. 4 also shows the optical fiber 14 residing in a groove 78 extending along the proximal portion 48A, the tapered portion 48E and the distal portion 48C of the core wire 48. If the groove 78 is large enough, the gap 66 discussed above with respect to the guidewire 12 may not be needed. Instead, the groove 78 provides enough room for the optical fiber 14 to move out of axial alignment as the guidewire 12 bends through a vasculature.

As shown in FIGS. 2, 2A and 3, the optical fiber 14 having the fiber cores 20, 22 and 24 extends along the core wire 48 and the intermediate housing 50 where the optical fiber terminates. That way, a distal end 14A of the optical fiber 14 is substantially aligned with a distal face 50G (FIG. 3) of the housing 50, perpendicular to the longitudinal axis A-A. Alternately, the distal end 14A of the optical fiber is recessed or proud with respect to the distal face 50G of the housing.

Figure 4A:
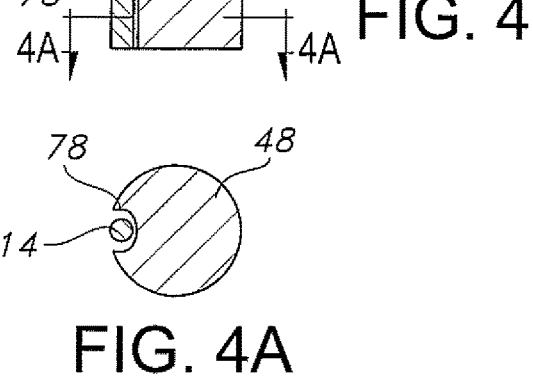
FIG. 4A is a cross-sectional view taken along line 4A-4A of FIG. 4.
Figure 5:
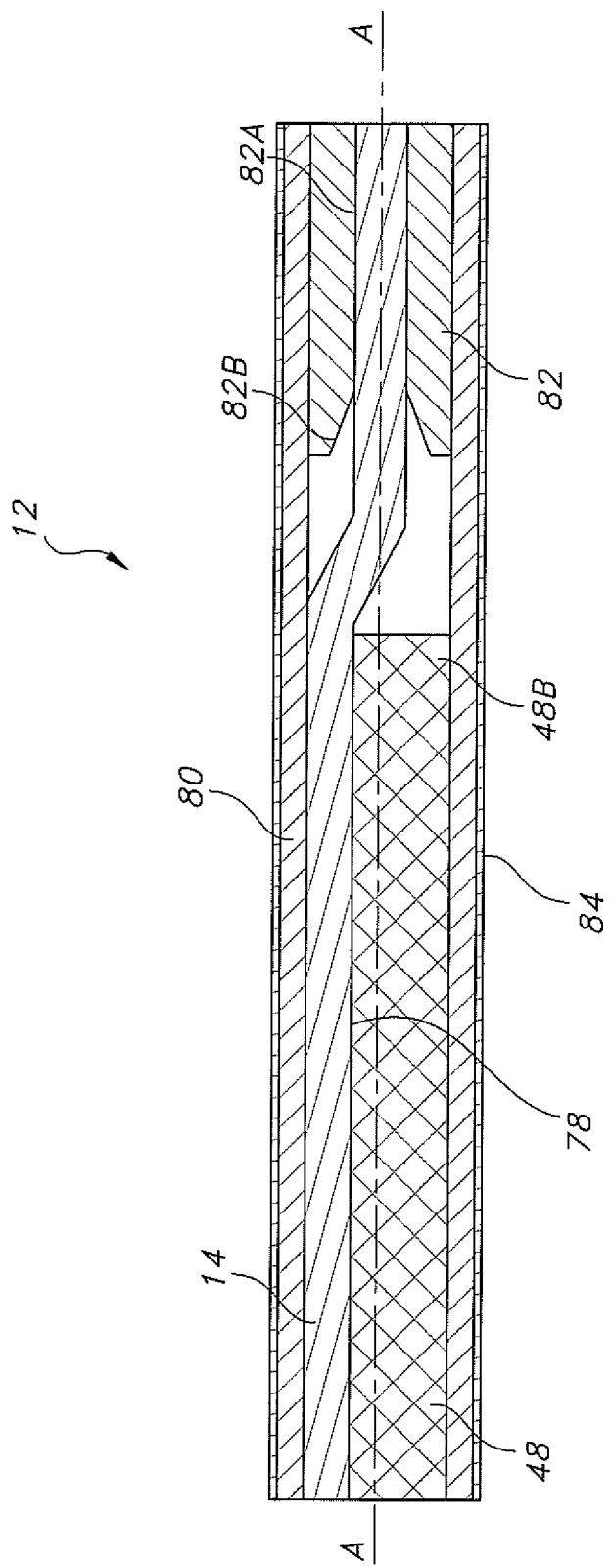
FIG. 5 is a cross-sectional view of the proximal end of the guidewire 12 shown in FIGS. 2, 4 and 4A with the optical fiber 14 supported in the groove 78 of the core wire 48 and having its proximal end connected to a proximal ferrule 82 residing in a proximal hypotube 80.

FIG. 5 shows the proximal end of the guidewire 12 with the core wire 48 supporting the optical fiber 14. The proximal end 48B of the core wire 48 resides inside and is connected to a cylindrically-shaped proximal hypotube 80. A ferrule 82 is also supported inside the hypotube 80, spaced proximally from the proximal end 48B of the core wire 48. The ferrule 82 is a cylindrically-shaped member having a lumen 82A extending to a taper 82B. The optical fiber 14 residing in the groove 78 in the core wire 48 shown in FIGS. 4 and 4A resides in this lumen 82A. The ferrule taper 86B aids in making this connection.

Preferably, a lubricious coating 84 is provided on the hypotube 80 and on exposed portions of the core wire 48, the housing 50, the hypotube 54/spring 54A subassembly and the atraumatic head 56 as well. The lubricious coating 84 helps to reduce friction between the guidewire 12 and body tissue as the guidewire 12 is moved through a vasculature. Suitable coatings for this purpose are described in U.S. Pat. No. 9,255,173 to Edwards, U.S. Pat. No. 9,623,157 to Edwards, U.S. Pat. No. 9,714,361 to Edwards, and U.S. Pat. No. 10,899,944 to Edwards, and in U.S. Pub. Nos. 2014/0275340 to Edwards and 2016/0160078 to Edwards, all of which are assigned to the assignee of the present invention and incorporated herein by reference. Suitable lubricious coatings are also described in U.S. Pat. No. 7,776,956 to Webster at al. and U.S. Pat. No. 9,676,895 to Harkal et al.

Figure 6:
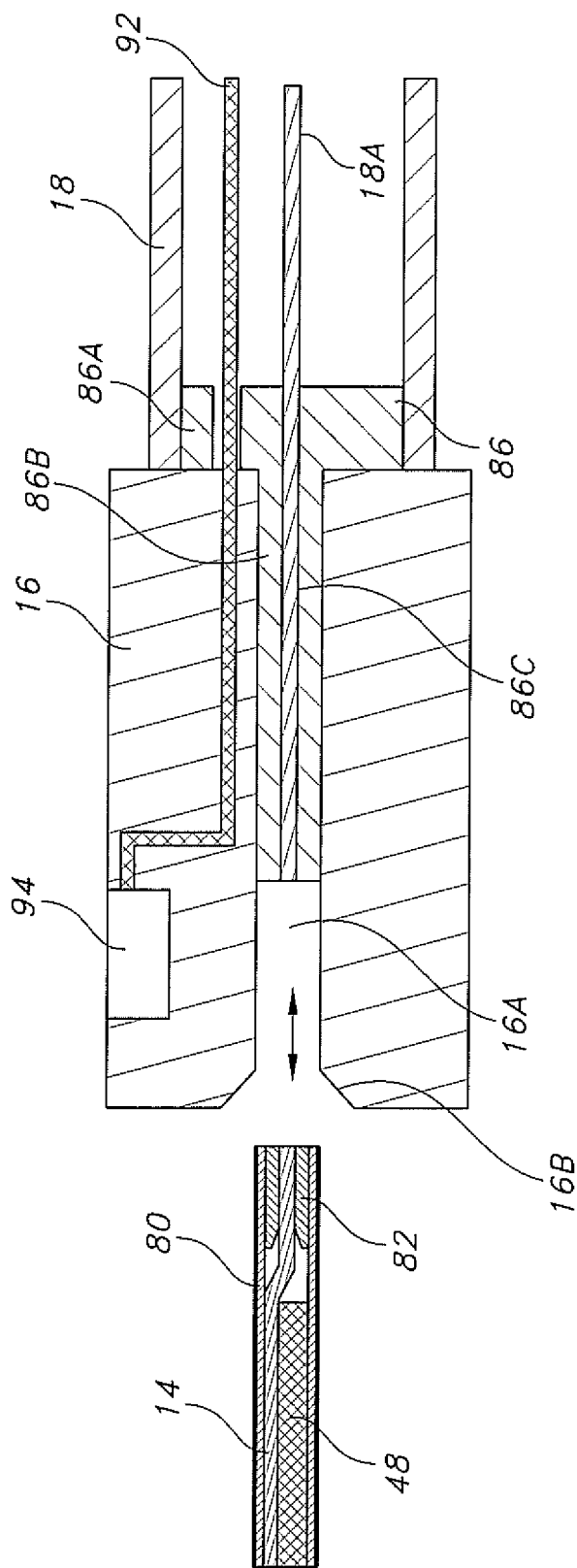
FIG. 6 is a schematic view of the guidewire 12 shown in FIGS. 1 and 5 being moved into the optical connector 16 of the guidewire system 10.

FIG. 6 illustrates the guidewire 12 being moved into the optical connector/handle 16 shown in FIG. 1. The optical connector 16 has a lumen 16A extending to a distal taper 16B. An insert 86 has an enlarged head 86A connected to a distal ferrule 86B. A lumen 86C extends through the enlarged head 86A and ferrule 86B of the connector insert 86. The distal end of the optical fiber 18A of the external optical cable 18 resides in the distal ferrule 86B of the insert 86 with the distal ferrule 86B in turn residing in the connector lumen 16A. A strain-relief sleeve 88 (FIGS. 1 and 8) adds support to the external optical cable 18 and helps prevent wear and chafing of the cable against the optical connector 16.

Figure 7:
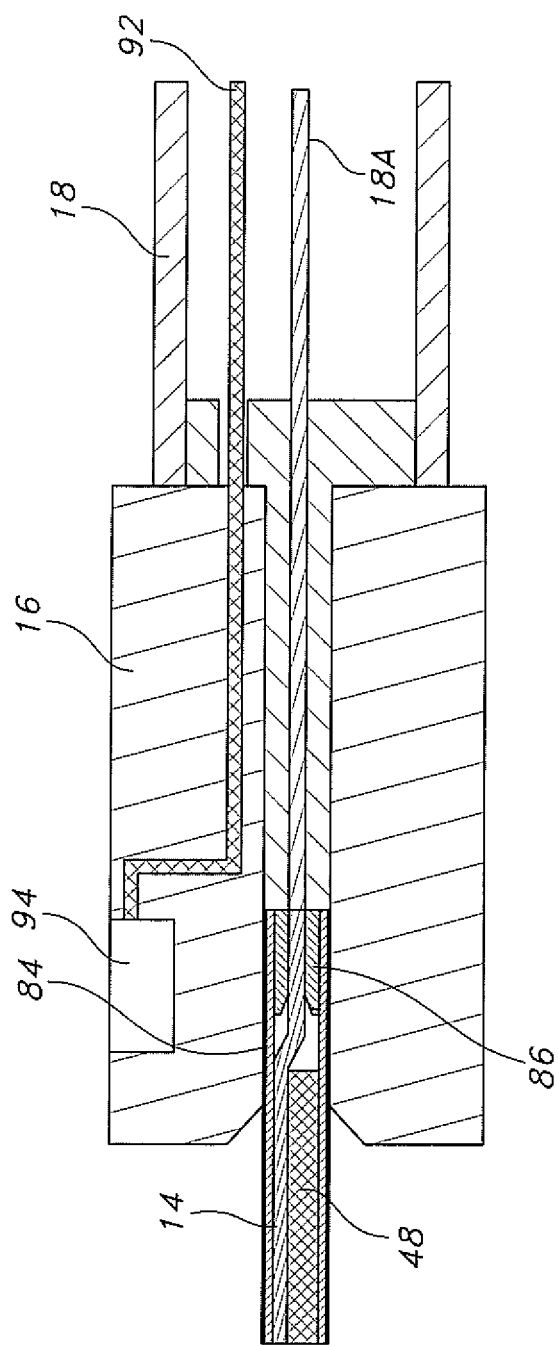
FIG. 7 is a schematic view of the guidewire 12 shown in FIGS. 1 and 5 with the optical fiber 14 now being optically connected to an external optical cable 18 in the optical connector 16.

FIG. 7 shows the optical fiber 14 of the guidewire 12 optically connected to the external optical cable 18 in the connector/handle 16. In the optical connector 16, the fiber cores 20, 22 and 24 of the guidewire optical fiber 14 are optically connected to the respective external fiber cores 20A, 22A and 24A comprising the optical fiber 18A of the external optical cable 18.

Figure 8:
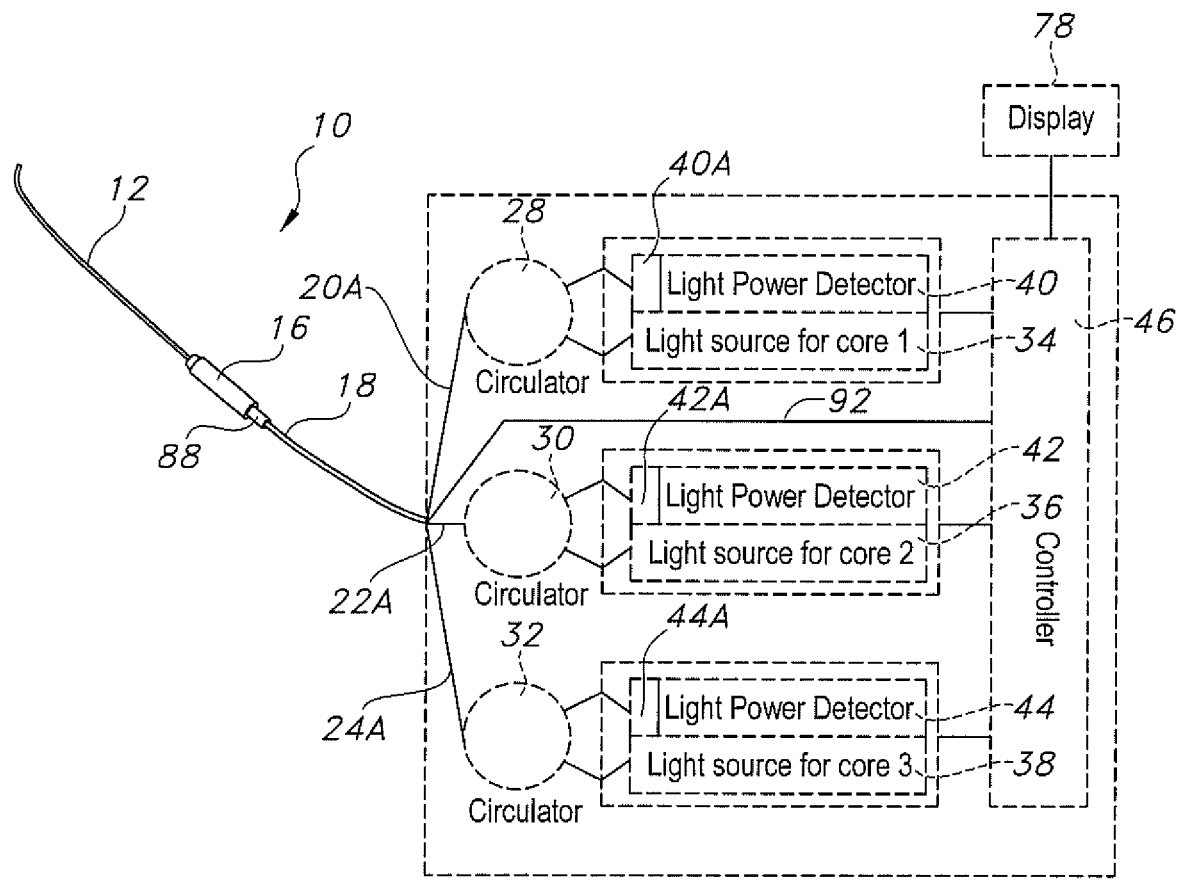
FIG. 8 is a schematic of the guidewire system 10 shown in FIG. 1 including the optical fiber 14 supporting fiber cores 20, 22 and 24 optically connected to respective light sources 34, 36, 38 and 39 and light power detectors 40, 42 and 44.

As schematically shown in FIG. 8, the external fiber cores 20A, 22A and 24A are optically connected to dedicated light sources 34, 36 and 38. More specifically, fiber core 20A is optically connected to a first light source 34, fiber core 22A is optically connected to a second light source 36, and fiber core 24A is optically connected to a third light source 38.

The first light source 34 emits light of a first power through a first circulator 28 into the external fiber core 20A optically connected to the fiber core 20 of the optical fiber 14 in the guidewire 12. Similarly, the second light source 36 emits light of a second power through a second circulator 30 into the external fiber core 22A optically connected to the fiber core 22 of the optical fiber 14. Further, the third light source 38 emits light of a third power through a third circulator 32 into the external fiber core 24A optically connected to the fiber core 24 of the optical fiber 14.

In various embodiments, the light sources 34, 36 and 38 are single wavelength light sources, narrow-band wavelength light sources or broadband wavelength light sources. However, to prevent light from one fiber core from being reflected into a different fiber core and this power then being measured and input into the controller 46, each fiber core is irradiated with light of a different wavelength (or band of wavelengths) that does not overlap with the light wavelengths irradiating any of the other fiber core. The light power detector for each fiber core is only sensitive to the specific light wavelength of its corresponding fiber core.

Moreover, as shown in FIG. 8, in an exemplary embodiment of the present guidewires 12, 12A, each light power detector 40, 42 and 44 is provided with a filter 40A, 42A and 44A that allows only the correct wavelength or band of wavelengths through to the controller 46. The important aspect of this embodiment is that each of the filters 40A, 42A and 44A does not allow any light through that will overlap with the detected light wavelengths of the other filters. Each light source 34, 36 and 38 irradiates its corresponding fiber core 20, 22 and 24 with light of a different wavelength or wavelengths matching the filter 40A, 42A and 44A of the associated power detector 40, 42 and 44. Then, so long as the respective light power detector 34, 36 and 38 is sensitive to the incoming light power, and the detector is configured to output a current or voltage that correlates with the power collected through the respective fiber core pairs 20/20A, 22/22A and 24/24A, the controller 46 is programmed to calculate the magnitude and vector of force imparted to the atraumatic head 56 and hence the special orientation of the guidewire 12, 12A in the vasculature. A narrow linewidth laser is suitable for the dedicated light sources 34, 36 and 38. A Superluminescent Light Emitting Diode (SLED) or a scanning laser is a suitable broadband light source.

In another embodiment, there is only one broadband light source that selectively emits light into each external fiber core 20A, 22A and 24A optically connected to the respective fiber cores 20, 22 and 24 of the optical fiber 14.

Regardless whether the light sources 34, 36 and 38 are dedicated light sources or the broadband light sources, light reflected by the mirror 72 onto the distal face 14A of the optical fiber 14 returns via the fiber cores 20, 22 and 24 to the connector 16 and the respective external fiber cores 20A, 22A and 24A and then the respective circulators 28, 30 and 32. The circulators 28, 30 and 32 are optically connected to corresponding light power detectors 40, 42 and 44. Each detector analyzes the light it receives to identify the intensity of the light at various powers. As will be described in greater detail hereinafter, this information is forwarded to the controller 46 where the difference in the intensity of the reflected light and then the percentage of the reflected light that is captured by the fiber cores 20, 22 and 24 with respect to the intensity of the light originally emitted by the light source into each fiber core 20, 22 and 24 is used to calculate the magnitude of the axial and lateral forces imparted to the atraumatic head 56 of the guidewire 12. The magnitude of the axial and lateral forces imparted to the atraumatic head 56 in turn is used to calculate the position of the atraumatic head 56 in the vasculature.

Figure 9:
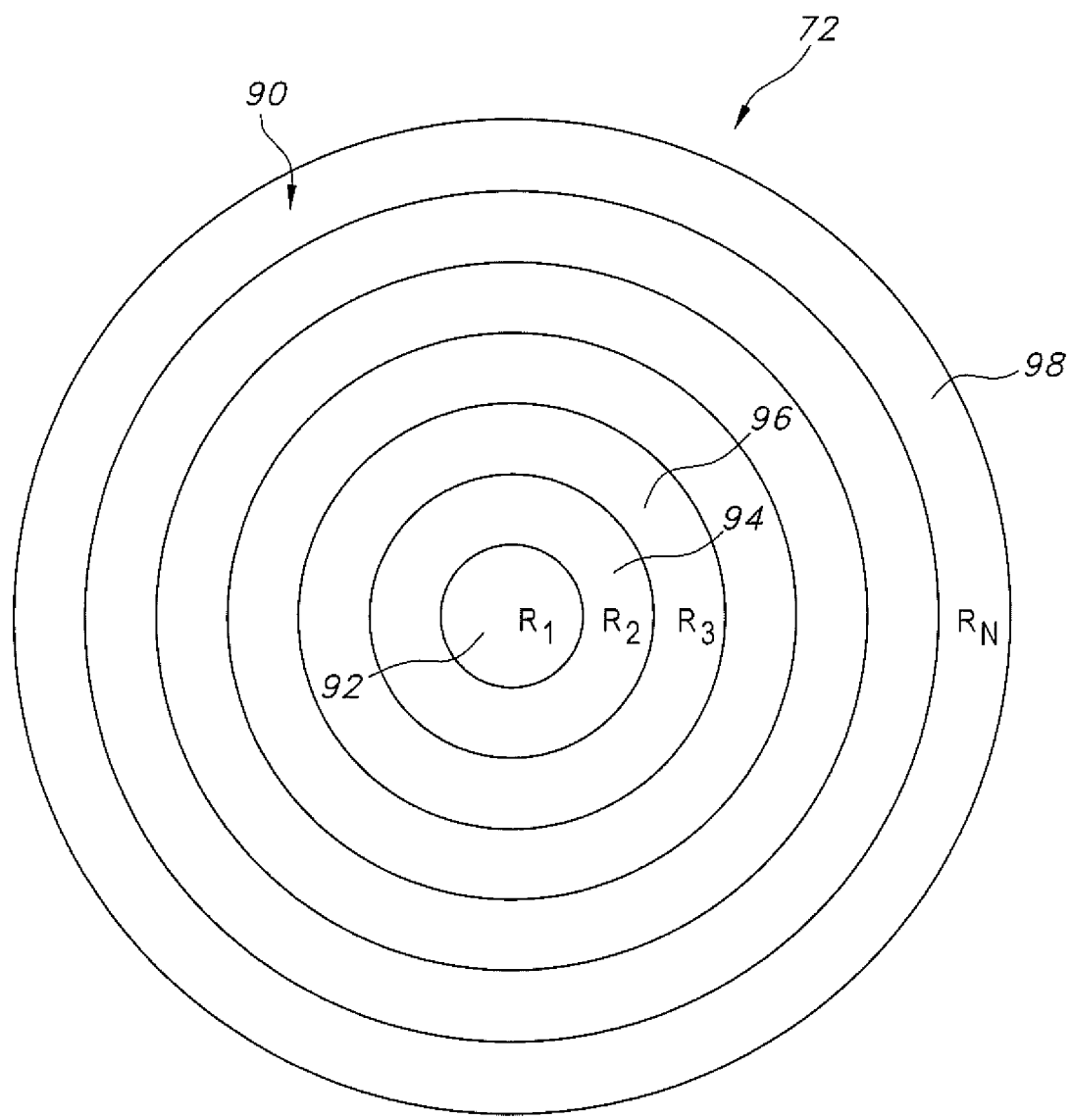
FIG. 9 is a plan view of the reflective surface 90 of the mirror 72 patterned so that light reflectance varies along a radius radiating outwardly from a central area of light reflectivity 92.

FIG. 9 illustrates an embodiment of the present guidewires 12, 12A that increases the accuracy of the positional measurement of the atraumatic head 56. In this embodiment, the mirror 72 is provided with a reflective surface 90 that is patterned so that light reflectivity or light reflectance (the light reflective quality or power of the reflective surface 90) varies along a radius radiating outwardly from a central area of light reflectivity 92. The reflectance of the mirror 72 is its effectiveness in reflecting radiant energy. It is the fraction of incident electromagnetic power that is reflected at the mirror 72. Reflectance is a component of the response of the electronic structure of the mirror 72 to the electromagnetic field of light, and is in general a function of the frequency, or wavelength, of the light, its polarization, and the angle of incidence. The dependence of reflectance on the wavelength is called a reflectance spectrum or spectral reflectance curve.

In that manner, the first or central area of light reflectivity 92 has a first light reflectivity $R_1$. A first annular band or ring 94 at a first radial distance from the central area of light reflectivity 92 has a second light reflectivity $R_2$, which is different than the first light reflectivity $R_1$. A second annular ring 96 at a second radial distance from the central area of light reflectivity 92 has a third light reflectivity $R_3$, which is different than the first light reflectivity $R_1$ of the central area 92 and the second light reflectivity $R_2$ of the first annular ring 94. This pattern continues radially across the reflective surface 90 of the mirror 72 to an outermost annular ring 98 having an nth light reflectivity $R_n$ that is different than the first, second and third light reflectivities $R_1$, $R_2$ and $R_3$ of the respective central area 92, first annular ring 94 and second annular ring 96.

The pattern of varying reflectance of the reflective surface 90 of the mirror 72 can be fabricated in the following ways:

a) patterned surface roughening by a laser robotically directed onto the regions to be roughened and controlled by software;

b) surface roughening by applying photoresist, patterning the photoresist using a mask, removing photoresist in the required areas and etching those areas to roughen the reflective surface 90; and c) depositing either reflection or anti-reflection coatings onto the mirror 72 and then selectively removing the coating in the required area using masking techniques.

It is noted that the reflective surface 90 of the mirror 72 shown in FIG. 9 has six annular rings radiating outwardly from the central area of reflectivity 92. However, that is meant for illustration and should not be taken as limiting the present invention. According to the present invention, there can be more than or less than six annular rings radiating outwardly from a center area of reflectivity. Moreover, the central area of reflectivity need not be circular. If desired, it can have a different shape, for example, a square shape or be a multi-sided closed plane bounded by straight lines (polygon).

Figure 10:
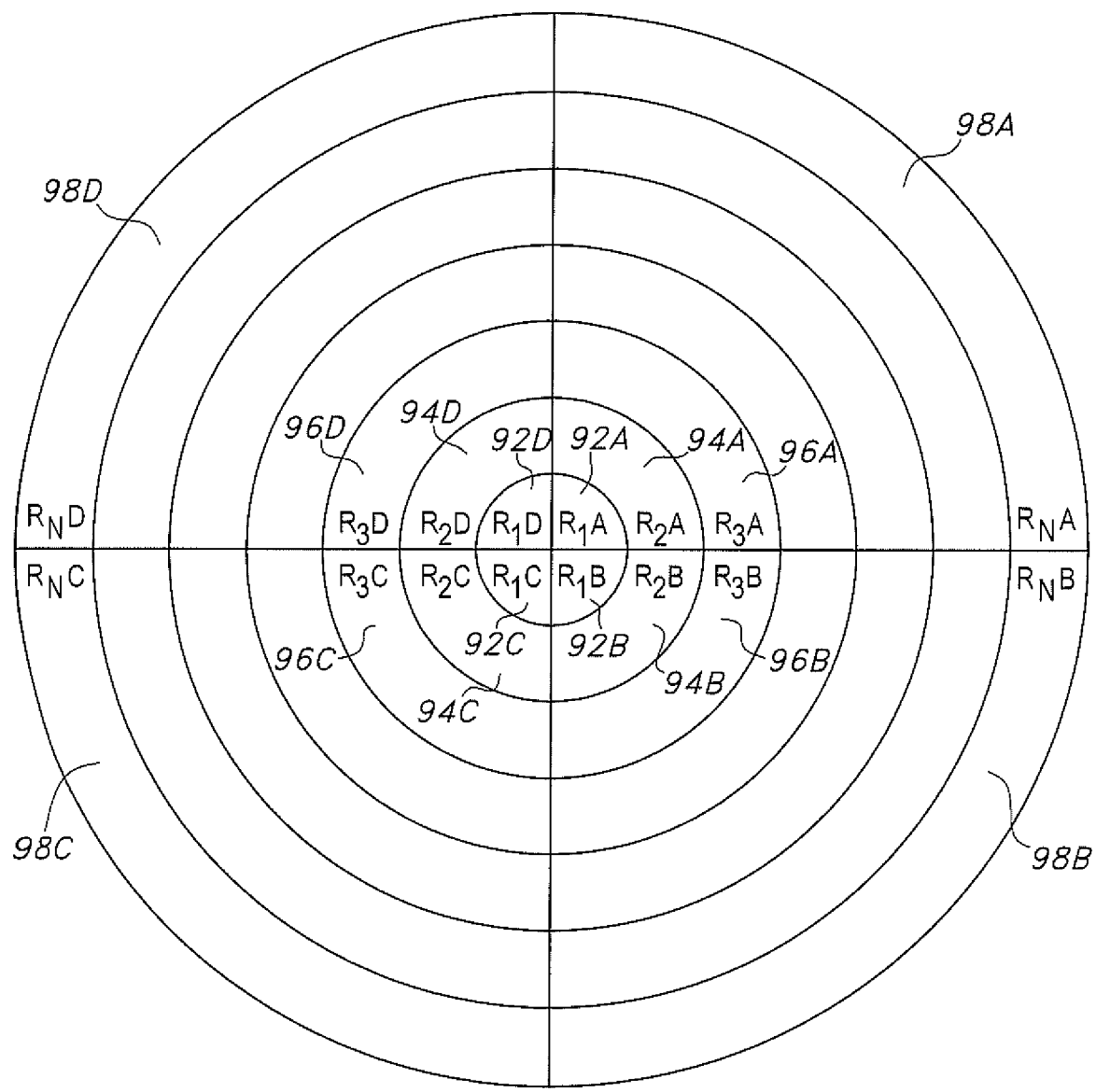
FIG. 10 is a plan view of the reflective surface 92 of the mirror 72 shown in FIG. 9, but with the patterned light reflectances divided into quadrants.

FIG. 10 illustrates an embodiment of the mirror 72 for the guidewires 12, 12A of the present invention that further increases the accuracy of the positional measurement of the atraumatic head 56. In this embodiment, the reflective surface 90 of the mirror 72 comprises the center or first area of light reflectivity 92 having the first light reflectivity $R_1$, the outwardly radiating annular bands or rings 94, 96 having the respective second and third light reflectivities $R_2$ and $R_3$ and continuing to the outermost annular ring 98 of the nth light reflectivity R. However, in this embodiment, the center or first area of light reflectivity 92, the first and second annular rings 94, 96 continuing to the nth annular ring 98 are each divided into quadrants.

Specifically, the first light reflectivity $R_1$ of the central area of light reflectivity 92 is divided into a first quadrant 92A of the first light reflectivity $R_1A$, a second quadrant 92B of the first light reflectivity $R_1B$, a third quadrant 92C of the first light reflectivity $R_1C$, and a fourth quadrant 92D of the first light reflectivity $R_1D$. Each of the light reflectivities $R_1A$, $R_1B$, $R_1C$ and $R_1D$ of the respective quadrants 92A, 92B, 92C and 92D is different than the other light reflectivities. The respective light reflectivities are input into the programmable memory of the controller 46.

Similarly, the second light reflectivity $R_2$ of the first ring of light reflectivity 94 is divided into a first quadrant 94A of the second light reflectivity $R_2A$, a second quadrant 94B of the second light reflectivity $R_2B$, a third quadrant 94C of the second light reflectivity $R_2C$, and a fourth quadrant 94D of the second light reflectivity $R_2D$. Each of the light reflectivities $R_2A$, $R_2B$, $R_2C$ and $R_2D$ of the respective quadrants 94A, 94B, 94C and 94D is different with respect to each other and with respect to the light reflectivities $R_1A$, $R_1B$, $R_1C$ and $R_1D$ of the respective quadrants 92A, 92B, 92O and 92O of the central area of light reflectivity 92. The respective light reflectivities are input into the programmable memory of the controller 46.

Further, the third light reflectivity $R_3$ of the second ring of light reflectivity 96 is divided into a first quadrant 96A of the third light reflectivity $R_3A$, a second quadrant 96B of the third light reflectivity $R_3B$, a third quadrant 96C of the third light reflectivity $R_3C$, and a fourth quadrant 96D of the third light reflectivity $R_3D$. Each of the light reflectivities $R_3A$, $R_3B$, $R_3C$ and $R_3D$ of the respective quadrants 96A, 96B, 96C and 96O is different with respect to each other and with respect to the light reflectivities $R_2A$, $R_2B$, $R_2C$ and $R_2D$ of the respective quadrants 94A, 94B, 94C and 94D of the first ring of light reflectivity 94 and with respect to the light reflectivities $R_1A$, $R_1B$, $R_1C$ and $R_1D$ of the respective quadrants 92A, 92B, 92C and 92D of the central area of light reflectivity 92. The respective light reflectivities are input into the programmable memory of the controller 46.

This pattern continues across the reflective surface 90 of the mirror 72 to the nth light reflectivity $R_n$ of the outermost ring of light reflectivity 98. The nth light reflectivity $R_n$ of the outermost ring of light reflectivity 98 is divided into a first quadrant 98A of the nth light reflectivity $R_nA$, a second quadrant 98B of the nth light reflectivity $R_nB$, a third quadrant 98C of the nth light reflectivity $R_nC$, and a fourth quadrant 98D of the nth light reflectivity $R_nD$. Each of the light reflectivities $R_nA$, $R_nB$, $R_nC$ and $R_nD$ of the respective quadrants 98A, 98B, 98C and 98D is different with respect to each other and with respect to the light reflectivities $R_3A$, $R_3B$, $R_3C$ and $R_3D$ of the respective quadrants 96A, 96B, 96C and 96D of the second ring of light reflectivity 96, with respect to the light reflectivities $R_2A$, $R_2B$, $R_2C$ and $R_2D$ of the respective quadrants 94A, 94B, 94C and 94D of the first ring of light reflectivity 94 and with respect to the light reflectivities $R_1A$, $R_1B$, $R_1C$ and $R_1D$ of the respective quadrants 92A, 92B, 92C and 92D of the central area of light reflectivity 92. This pattern continues across the reflective surface 90 of the mirror 72 for as many rings of light reflectivity as the mirror 72 has. The respective light reflectivities are input into the programmable memory of the controller 46.

Figures 11A, 11B:
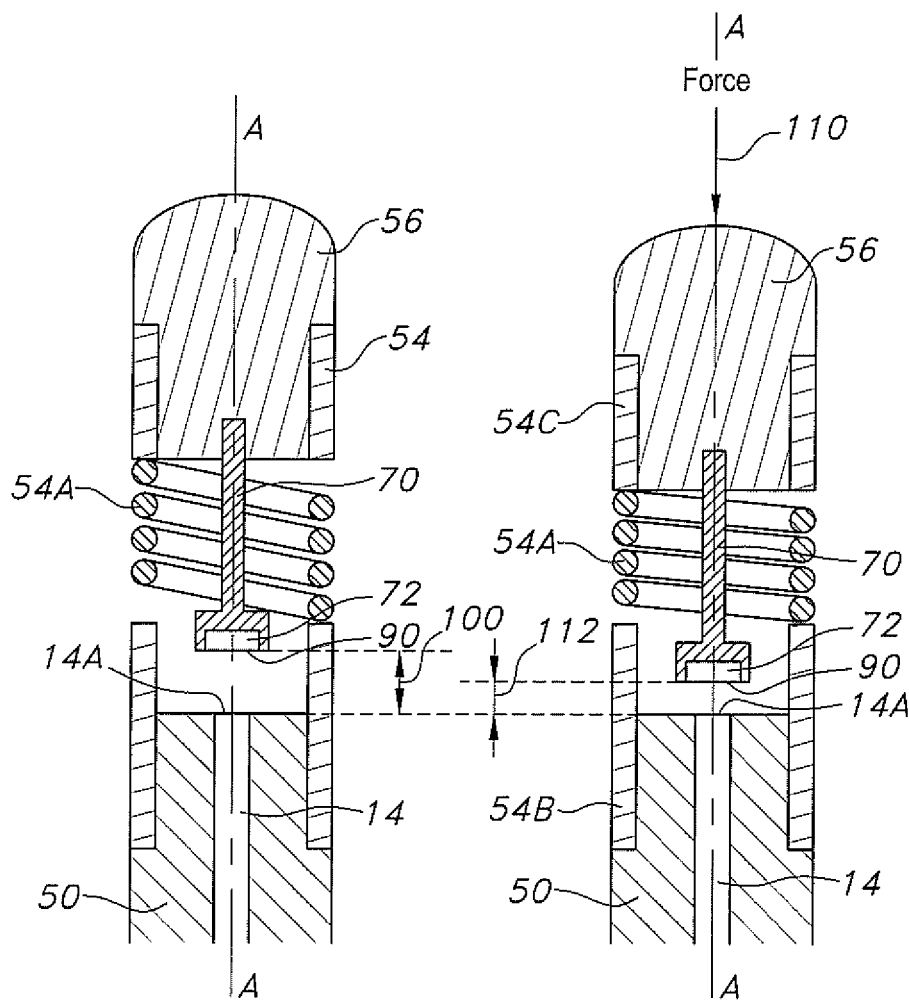
FIGS. 11A and 11b are respective cross-sectional views showing the relative position of the mirror 72 with respect to the distal face 14A of the optical fiber 14 without and with an axial force imparted to the atraumatic head 56.

FIG. 11A illustrates the guidewire 12, 12A in a first or neutral state without any axial or lateral force imparted to the atraumatic head 56. In this orientation, the distance between the distal face 14A of the optical fiber 14 and the reflective surface 90 of the mirror 72 is indicated by arrow 100. In the neutral state, light emitted by the light sources 34, 36 and 38 into a respective one of the fiber core pairs 20A/20, 22A/22 and 24A/24 results in a conical beam emerging from the fiber core and results in a circular area of light shining on the reflective surface 90.

Figures 12A, 12B:
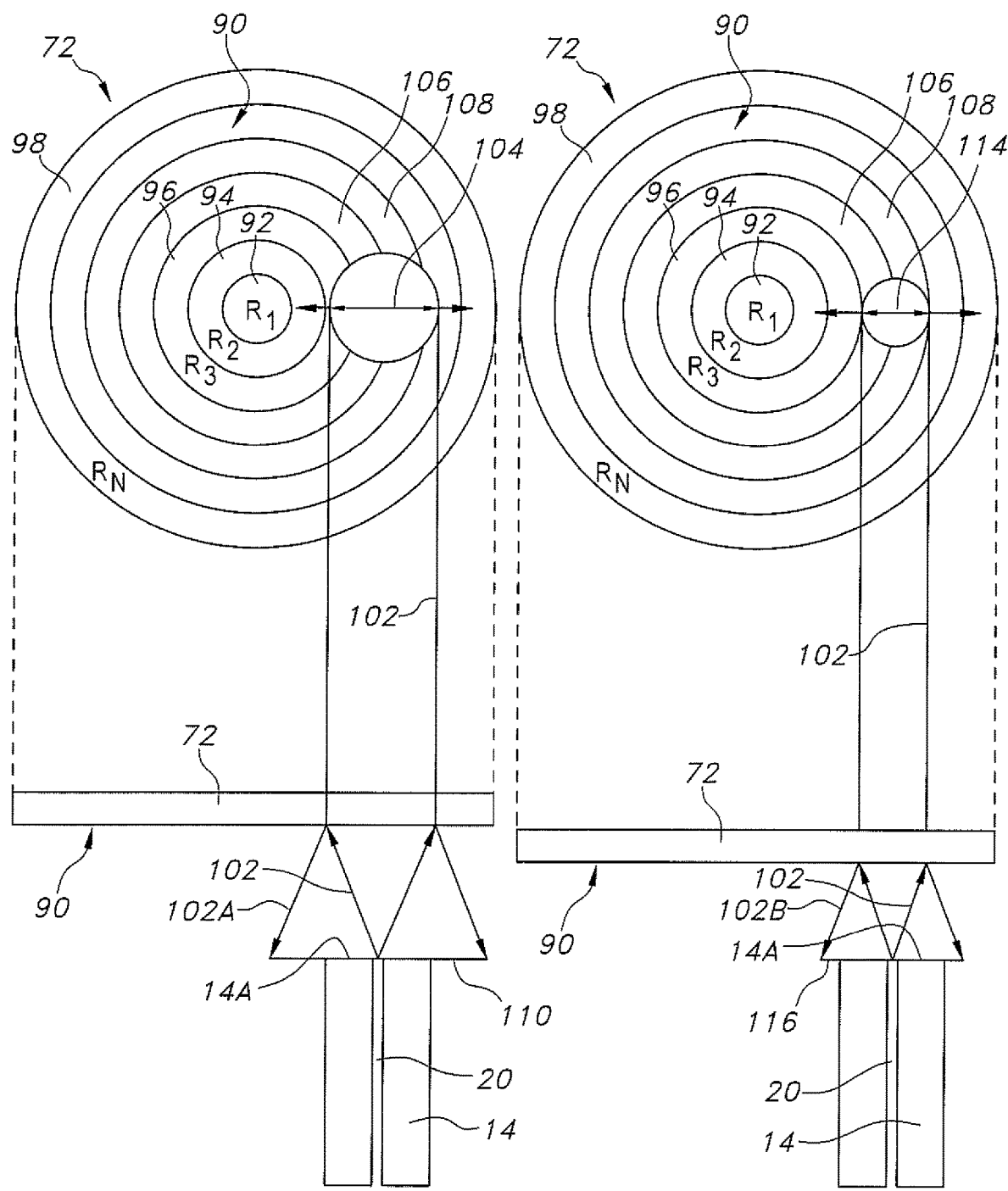
FIGS. 12A and 12B are respective plan views of light shining on the reflective surfaces 90 of the mirrors 72 shown in FIGS. 11A and 11B.

This is illustrated in FIG. 12A where one of the fiber cores, for example, fiber core 20 is shown shining a conical light beam 102 that impinges on the reflective surface 90 of the mirror 72. The light beam 102 has a circular intensity or power profile in the plane perpendicular to the longitudinal axis A-A with a diameter at the reflective surface 90 of the mirror 72 indicated by arrow 104 that is approximately centered at the delineation between a third annular ring of reflectance 106 and a fourth annular ring 108 of reflectance. The reflective surface 90 of the mirror 72 reflects a reflected percentage 102A of the power of the conical light beam 102 back toward the distal face 14A of the optical fiber 14. The conically divergent reflected percentage 102A of the light beam 102 has a circular intensity or power profile perpendicular to the axis with a diameter at the distal face 14A of the optical fiber indicated by line 110.

Since the light beam 102 from representative fiber core 20 is still approximately centered at the delineation between the third and fourth annular rings of reflectance 106, 108, different reflected percentages will reflect off each of those surfaces 106, 108. Then, a percentage of the reflected percentage 102A off each of the annular rings of reflectance 106, 108 is captured by the fiber core 20 and travels along the optical fiber 14, through the connector 16 to the external fiber core 20A optically connected to the light power detector 40 and then the controller 46 shown in FIG. 8. The light power detector 40 detects the power of the light captured by the fiber core 20 following reflection off the annular rings of reflectance 106, 108 and sends that information to the controller 46. The annular rings of reflectance 106, 108 reflect different percentages of the power of the light beam 102, which the light power detector 40 is programmed to detect. The controller is further programmed to use the captured percentage of the reflected percentage 102A off each of the annular rings of reflectance 106, 108 as an input to calculate the position of the reflective surface 90 and output to the display 78 that no axial or lateral forces are imparted to the atraumatic head 56.

Similar principals apply regarding the reflectances of the light reflectivities $R_1$, $R_2$, $R_3$ and $R_n$ of the respective central area 92, the first annular ring 94, the second annular ring 96 and the nth annular ring 98 shown in FIG. 9, and with respect to the light reflectivities $R_1A$, $R_1B$, $R_1C$ and $R_1D$ of the respective quadrants 92A, 92B, 92C and 92D of the central area of light reflectivity 92, the light reflectivities $R_2A$, $R_2B$, $R_2C$ and $R_2D$ of the respective quadrants 94A, 94B, 94C and 94D of the first ring of light reflectivity 94, the light reflectivities $R_3A$, $R_3B$, $R_3C$ and $R_3D$ of the respective quadrants 96A, 96B, 96C and 96D of the second ring of light reflectivity 96, and the light reflectivities $R_nA$, $R_nB$, $R_nC$ and $R_nD$ of the respective quadrants 98A, 98B, 98C and 98D of the nth ring of light reflectivity shown in FIG. 10.

FIG. 11B illustrates the guidewire 12, 12A in a second state with only an axial force 110 but no lateral force imparted to the atraumatic head 56. In this orientation, the distance between the distal face 14A of the optical fiber 14 and the reflective surface 90 of the mirror 72 is indicated by numerical designation 112, which is less than distance 100 in FIG. 11A. In this second state, a reflected percentage 102B of the light shining from the fiber cores 20, 22 and 24 is reflected by the reflective surface 90 of the mirror 72 back to the distal face 14A of the optical fiber 14.

Referring still to FIG. 11B, the axial force vector 110 is shown causing the spring 54A to compress, which in turn causes the reflective surface 90 of the mirror 72 to move proximally along the longitudinal axis A-A so that the mirror 72 is closer to the distal face 14A of the optical fiber 14 than in the neutral state shown in FIG. 11A with no axial or lateral force imparted to the atraumatic head 56. This axial movement of the mirror 72 results in a reflected percentage 102B of the power of the conical light beam 102 shining toward the distal face 14A of the optical fiber 14. The intensity profile of the reflected percentage 102B has a diameter indicated by line 116 reflected toward the plane of the distal face 14A of the optical fiber 14 in FIG. 12B. While line 116 has a smaller diameter than line 110 in FIG. 12A, the intensity of the reflected percentage 102B at the distal face of the optical fiber is greater than the intensity of the reflected percentage 102A at the distal face of the optical fiber shown in FIG. 12A because the mirror 72 is closer to the distal face 14A of the optical fiber 14. Then, a percentage of the reflected percentage 102B is captured by the fiber core 20 and travels along the optical fiber 14, through the connector 16 to the external fiber core 20A optically connected to the light power detector 40 and then the controller 46 shown in FIG. 8. The controller 46 is programmed to determine the difference in the intensity or power between the reflected percentages 102B and 102A captured by the fiber core with the position of the mirror 72 in FIG. 12B with respect to the position of the mirror 72 in FIG. 12A. The controller is programmed to use that difference as an input to calculate the position of the reflective surface 90 and output to the display 78 that an axial force and its magnitude, but no lateral force, is imparted to the atraumatic head 56.

However, since the light beam 102 from representative fiber core 20 is still approximately centered at the delineation between the third and fourth annular rings of reflectance 106, 108, different reflected percentages will reflect off each of the annular rings of reflectance 106, 108. Then, a percentage of the reflected percentage 102A off each of the annular rings of reflectance 106, 108 is captured by the fiber core 20 and travels along the optical fiber 14, through the connector 16 to the external fiber core 20A optically connected to the light power detector 40 and then the controller 46 shown in FIG. 8. The light power detector 40 detects the power of the light captured by the fiber core 20 off each of the annular rings of reflectance 106, 108 and sends that information to the controller 46. The annular rings of reflectance 106, 108 reflect different percentages of the power of the light beam 102, which the light power detector 40 is programmed to detect. The controller is further programmed to use the captured percentage of the reflected percentage 102A off each of the annular rings of reflectance 106, 108 as an input to calculate the position of the reflective surface 90 and output to the display 78 that only an axial force but no lateral force is imparted to the atraumatic head 56. Since the mirror 72 is closer to the distal face 14A of the optical fiber 14, the intensity or power of the reflected percentages from the annular rings of reflectance 106 and 108 is somewhat greater than in the configuration shown in FIGS. 11A and 12A.

Similar principals apply regarding the reflectances of the light reflectivities $R_1$, $R_2$, $R_3$ and $R_n$ of the respective central area 92, the first annular ring 94, the second annular ring 96 and the nth annular ring 98 shown in FIG. 9, and with respect to the light reflectivities $R_1A$, $R_1B$, $R_1C$ and $R_1D$ of the respective quadrants 92A, 92B, 92C and 92D of the central area of light reflectivity 92, the light reflectivities $R_2A$, $R_2B$, $R_2C$ and $R_2D$ of the respective quadrants 94A, 94B, 94C and 94D of the first ring of light reflectivity 94, the light reflectivities $R_3A$, $R_3B$, $R_3C$ and $R_3D$ of the respective quadrants 96A, 96B, 96C and 96D of the second ring of light reflectivity 96, and the light reflectivities $R_nA$, $R_nB$, $R_nC$ and $R_nD$ of the respective quadrants 98A, 98B, 98C and 98D of the nth ring of light reflectivity shown in FIG. 10.

Figure 13:
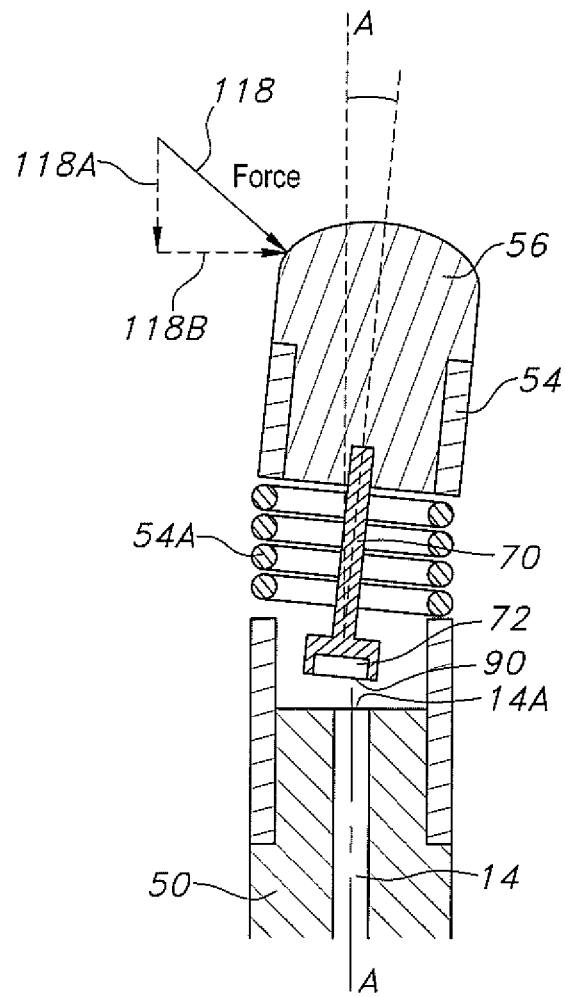
FIG. 13 is a cross-sectional view showing the mirror 72 when a force having both axial 118A and lateral 118B components is imparted to the atraumatic head 56.
Figures 13A, 13B:
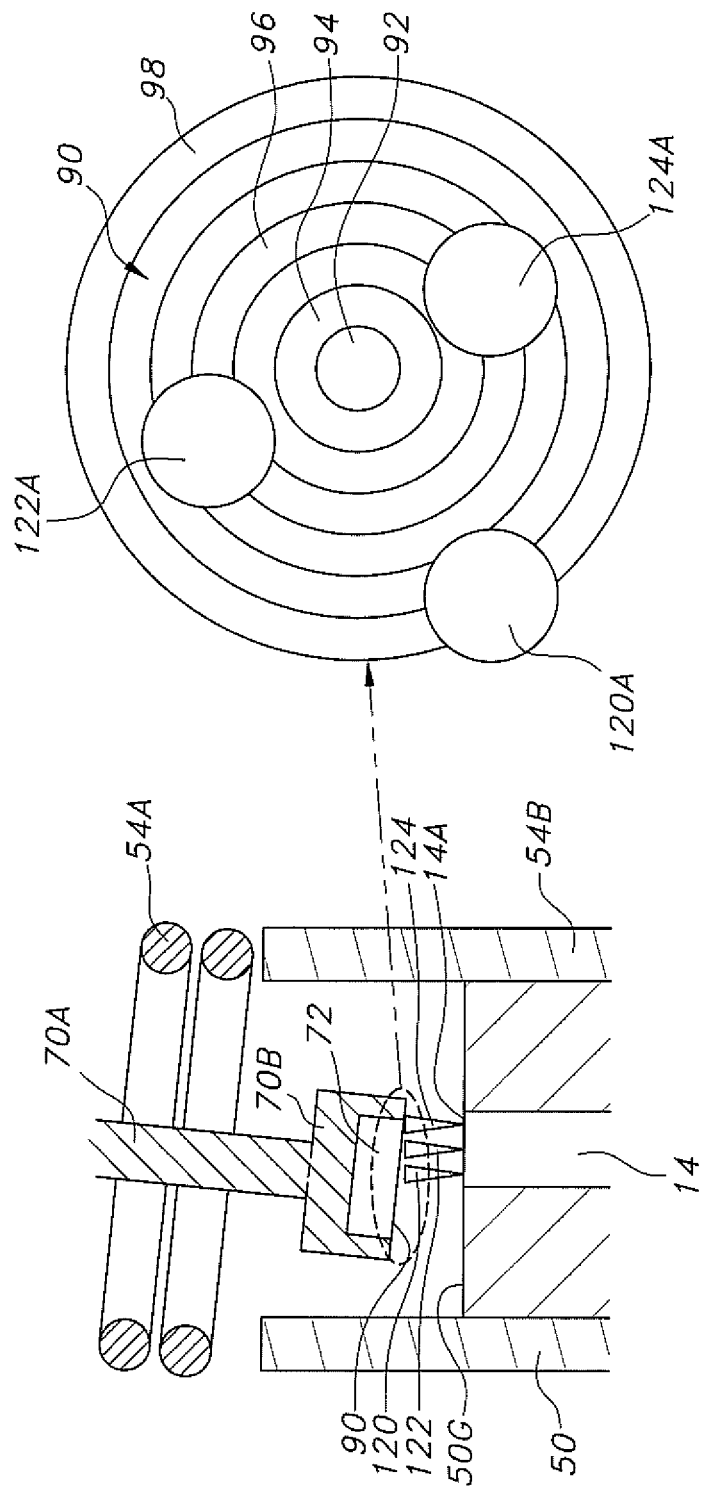
FIG. 13A is an enlarged cross-section view of the atraumatic head 56 and mirror 72 shown in FIG. 13 with light reflected from the mirror 72 to the optical fiber 14.
FIG. 13B is a plan view of the mirror 72 shown in FIGS. 13 and 13A with light impinging on its reflective surface 90.

FIG. 13 illustrates the atraumatic head 56 being subjected to a force vector 118 having an axial force component 118A and a lateral force component 118B. This causes the atraumatic head 56 to move laterally and axially with one portion of the spring 54A being compressed more than or less than a diametrically opposed portion of the spring. FIG. 13A is an enlarged view of FIG. 13 and shows the light beams 120, 122 and 124 that are emitted by the fiber cores 20, 22 and 24 shinning on the reflective surface 90 of the mirror 72. FIG. 132 illustrates the respective circular areas off shining light as light areas 120A, 122A and 124A. With no lateral force component (and either no axial force or only an axial force), the central area of light reflectivity 92 of the mirror 72 is centered equidistant between and with respect to the light areas 120A, 122A and 124A. However, this drawing shows that the shining light areas 120A, 122A and 124A have shifted on the reflective surface 90. The central area of reflectivity 92 is no longer centered between the shining light areas 120A, 122A and 124A. In fact, a portion of light 120A does not impinge on the reflective surface 90 at all.

Any change in the percentage of light captured by the fiber cores 20, 22 and 24 of the optical fiber 14 following reflection from the reflective surface 90 of the mirror 72 back to the distal face 14A of the optical fiber 14 and with respect to the percentages of light captured with the guidewire 12, 12A in the first state without an axial force being applied to the atraumatic head 56 or with respect to the reflected percentages of light captured with the guidewire 12, 12A in the second state with only an axial force but no lateral force being imparted to the atraumatic head 56 is indicative of forces of different axial and lateral magnitudes being applied to the atraumatic head. Then, relative change of the percentages of light captured by each of the cores 20, 22 and 24 is converted by the controller 46 into a value related to the force that the atraumatic head 56 is exerting against body tissue. The controller 46 is also programmed to calculate a spatial orientation in an x, y, z coordinate system of the atraumatic head 56 in the vasculature from the relative change of the percentage of light captured by each of the cores 20, 22 and 24.

Moreover, change in the percentage of light captured by the fiber cores 20, 22 and 24 of the optical fiber 14 following reflection from the reflective surface 90 of the mirror 72 back to the distal face 14A of the optical fiber 14 is with respect to the reflective surfaces shown in FIGS. 9 and 10 as described above for the state with no axial force imparted to the atraumatic head 56 shown in FIGS. 11A and 12A and with respect to the state with only an axial force but no lateral force imparted to the atraumatic head shown in FIGS. 11B and 12B.

While FIGS. 11A, 11B, 12A and 12B show a single representative fiber core 20, it is within the breadth and scope of the present invention that light reflecting off the reflective surface 90 of the mirror 72 (FIGS. 9 and 10) back to the fiber core, through the connector 16 to the external fiber core 20A and the light power detector 40 connected to the controller 46 with a single fiber core is illustrative of the optical principals of the present invention. Various embodiments of the optical fiber 14 are shown in FIGS. 1, 2A, 2B and 8 having three fiber cores 20, 22 and 24 with similar optical principals applying to each fiber core. Further, the present invention can be practiced with a guidewire having a plurality of fiber cores, for example, two fiber cores or more than three fiber cores. Moreover, if there is more than one fiber core, the fiber cores need not be evenly spaced about the circumference of the optical fiber 14. So long as the controller 46 is programmed with information related to the relative positions of the plurality of fiber cores, the optical principals described above apply.

In various embodiments of the present guidewires 12, 12A, the optical fiber 14 is a step index fiber, a graded index fiber or a photonic crystal fiber. In other embodiments of the present guidewires 12, 12A, the optical fiber 14 is a single-mode fiber, a multi-mode fiber, or a dual clad fiber could be used to deliver and capture the light. Still, in other embodiments of the present guidewires 12, 12A, a lens is placed between the distal face 14A of the optical fiber 14 and the mirror 72 to focus the light beam on the reflective surface 90 of the mirror.

In one embodiment of the present guidewires 12, 12A, the proximal end of the optical fiber 14 is uniformly illuminated by the light sources 34, 36 and 38 to equally excite all bound modes so that the near-field pattern of the emerging light at each of the fiber cores 20, 22 and 24 at the distal face 14A approximates the refractive index profile of the fiber core.

In another embodiment, the fiber cores 20, 22 and 24 each pass through a mode scrambler to achieve a uniformly distributed light beam.

Referring back to FIG. 8, this drawing illustrates that there is a visual display 78 connected to the controller 46. As described above, the controller 46 is programmed to calculate the spatial orientation of the atraumatic head 56 in the vasculature and the force that the atraumatic head is exerting against body tissue, for example, against an occlusion. Among other useful information, the display 78 presents this orientation and force information in real-time in any one of a variety of formats that are useful to the surgeon.

As previously described, during movement of the guidewire 12 through the vasculature (both forward and rearward movement), frictional feedback from the surface of the shaft of the guidewire dominates the tactile feel in the surgeon's hand while tactile perception of the force acting at the atraumatic head 56 is minimal. Therefore, there is a risk of vessel injury including perforation due to the force of the guidewire 12 including its atraumatic head 56 against the vasculature tissue.

To overcome this, axial and lateral forces applied to the atraumatic head 56 are not only fed back to the controller 46 for presentation by the display 78 as described above, but, as shown in FIG. 6, the controller also sends a haptic or tactile feedback signal through an electrical cable 92 to an electromechanical actuator 94 integrated into the connector/handle 16. Haptic or tactile feedback is the use of vibration patterns to convey information to a user or operator. Haptic feedback uses the controller 46 to send haptic feedback signals to the electromechanical actuator 94, which can be felt by the surgeon holding the connector 16. Exemplary electromechanical actuators include a vibration motor, an eccentric rotating mass (ERM) actuator driven by an electronic circuit, a linear resonant actuator, and a piezoelectric actuator.

In the guidewire system of the present invention, an exemplary embodiment has the vibration increase in frequency or amplitude depending on the calculated force of the atraumatic head 56 against vasculature tissue. Further, the vibrational frequency can be varied to indicate the direction of the force while the amplitude of the vibration can be varied to indicate the magnitude of the axial and lateral force vectors. That way, the surgeon feels the magnitude and direction of the axial and lateral force vectors in his hand as the atraumatic head 56 of the guidewire 12, 12A is moved through the vasculature during a medical procedure.

This haptic or tactile feedback to the surgeon helps reduce the risk of damaging tissue, speeds up the medical procedure and reduces contrast and x-ray use. Also, the haptic or tactile feedback correlates with the hardness of the tissue encountered by the atraumatic head 56. This helps reduce the x-ray requirement further. The force data at the occlusion also conveys information on the make-up of the occlusion, such as how calcified it is, which is an important consideration when making treatment decisions such as whether to insert a stent, or not.

It is appreciated that various modifications to the inventive concepts described herein may be apparent to those of ordinary skill in the art without departing from the spirit and scope of the present invention as defined by the appended claims.

What is claimed is:

1. A guidewire assembly, comprising:
   a) a guidewire, comprising:
      i) a core wire extending along a longitudinal axis from a core wire proximal end to a core wire distal portion having a core wire distal end, wherein a core wire lumen extends to the core wire proximal and distal ends;
      ii) a housing supported by the core wire distal portion, wherein a housing lumen extends to a distal end of the housing, the housing lumen being in open communication with the core wire lumen;
      iii) a distal hypotube providing a hypotube lumen extending from a hypotube proximal portion to a hypotube distal portion, wherein the hypotube proximal portion is supported by the housing, and wherein a distal spring is supported by the distal hypotube intermediate the hypotube proximal and distal portions;
      iv) an atraumatic head connected to the distal hypotube distal portion;
      v) an optical fiber extending through the core wire and housing lumens to the housing distal end, wherein at least one fiber core extends through the optical fiber to a distal face thereof; and vi) a mirror supported by the atraumatic head, wherein the mirror faces proximally but is spaced distally from the fiber core at the distal face of the optical fiber;
b) a light source optically connected to the optical fiber, wherein the light source is configured to emit light of a defined power into the fiber core;
c) a light power detector optically connected to the fiber core; and
d) a controller operatively coupled to the light power detector,
e) wherein, with the light source emitting light of the defined power into the fiber core shining at the mirror, and
f) wherein, in comparison to the guidewire with no axial or lateral forces imparted to the atraumatic head so that the atraumatic head is axially aligned with the core wire and the mirror is spaced a first distance from the distal face of the optical fiber and so that a reflected percentage of the light of the defined power is reflected by the mirror back to the distal face of the optical fiber with a first percentage of the reflected percentage of the defined light power captured by and traveling along the fiber core to the light power detector, the first percentage of the reflected percentage being determinable by the controller,
with only an axial force imparted to the atraumatic head of the guidewire to cause the atraumatic head to assume an orientation still axially aligned with the core wire but with the distal spring compressed so that the mirror is spaced a second distance from the distal face of the optical fiber, the second distance being less than the first distance, a second percentage of the reflected percentage of the defined light power is captured by and travels along the fiber core to the light power detector, the difference between the first and second percentages of the reflected percentage of the defined light power being determinable by the controller to calculate the magnitude of the axial force imparted to the atraumatic head, and
g) wherein, with both axial and lateral forces imparted to the atraumatic head of the guidewire to cause the atraumatic head and the distal spring of the distal hypotube to deflect out of axial alignment with the core wire and with respect to the distal face of the optical fiber, the mirror is spaced a third distance from the fiber core, the third distance being different than the first and second distances, so that in comparison to at least one of the first and second percentages of the reflected percentage of the defined light power, an axial and lateral force induced third percentage of the reflected percentage of the defined light power is captured by and travels along the fiber core to the light power detector, and wherein the controller is programmed to use the difference between the first and third percentages or the second and third percentages, or both, of the reflected percentage of the defined light power to calculate a magnitude and vector of the axial and lateral forces imparted to the atraumatic head.

2. The guidewire assembly of claim 1, wherein the mirror is provided with a patterned reflectance that varies along a radius from a central area of reflectance.

3. The guidewire assembly of claim 2, wherein the patterned reflectance of the mirror comprises the central area of reflectance having a first light reflectance $R_1$ and at least one annular ring of reflectance having a second light reflectance $R_2$, and wherein $R_1$ is different than $R_2$, and wherein the first percentages captured by and traveling along the fiber core of the reflected percentage of the defined light power reflected from the first and second light reflectances $R_1$ and $R_2$ of the mirror with no axial or lateral forces imparted to the atraumatic head in comparison to the second percentages captured by and traveling along the fiber core of the reflected percentage of the defined light power reflected from the first and second light reflectances $R_1$ and $R_2$ with only an axial force imparted to the atraumatic head is determinable by the controller to calculate the magnitude of the axial force imparted to the atraumatic head, and wherein the third percentages captured by and traveling along the fiber core of the reflected percentage of the defined light power reflected from the first and second light reflectances $R_1$ and $R_2$ of the mirror with both axial and lateral forces imparted to the atraumatic head in comparison to the first percentages captured by and traveling along the fiber core of the reflected percentage of the defined light power reflected from the first and second light reflectances $R_1$ and $R_2$ with no axial or lateral forces imparted to the atraumatic head or, in comparison to the second percentages captured by and traveling along the fiber core of the reflected percentage of the defined light power reflected from the first and second light reflectances $R_1$ and $R_2$ with only an axial force imparted to the atraumatic head is determinable by the controller to calculate the magnitude and vector of the axial and lateral forces imparted to the atraumatic head.

4. The guidewire assembly of claim 3, wherein the patterned reflectance of the mirror comprises the central area of reflectance having the first light reflectance $R_1$ and at least a first, a second and a third annular rings of reflectance having respective second, third and fourth light reflectances $R_2$, $R_3$ and $R_4$ at progressively greater first, second and third radial distances from the central area of reflectance, and wherein the light reflectances $R_1$, $R_2$, $R_3$ and $R_4$ are different from each other.

5. The guidewire assembly of claim 4, wherein the first light reflectance $R_1$ of the central area of reflectance and the second, third and fourth light reflectances $R_2$, $R_3$ and $R_4$ of the respective first, second and third annular rings of reflectance are each divided into quadrants of reflectance, and wherein the quadrants of reflectance of each of the light reflectances $R_1$, $R_2$, $R_3$ and $R_4$ are different from each other.

6. The guidewire assembly of claim 4, wherein the first light reflectance $R_1$ of the central area of reflectance of the mirror and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

7. A guidewire assembly, comprising:
a) a guidewire, comprising:
i) a core wire extending along a longitudinal axis from a core wire proximal end to a core wire distal portion having a core wire distal end, wherein a core wire lumen extends to the core wire proximal and distal ends;
ii) a housing supported by the core wire distal portion, wherein a housing lumen extends to a distal end of the housing, the housing lumen being in open communication with the core wire lumen;
iii) a distal hypotube providing a hypotube lumen extending from a hypotube proximal portion to a hypotube distal portion, wherein the hypotube proximal portion is supported by the housing, and wherein a distal spring is supported by the distal hypotube intermediate the hypotube proximal and distal portions;
iv) an atraumatic head connected to the distal hypotube distal portion;
v) an optical fiber extending through the core wire and housing lumens to the housing distal end, wherein at least a first fiber core, a second fiber core, and a third fiber core extend through the optical fiber to a distal face thereof; and
vi) a mirror supported by the atraumatic head, wherein the mirror faces proximally but is spaced distally from the first, second and third fiber cores at the distal face of the optical fiber;
b) at least one light source optically connected to the optical fiber, wherein the light source is configured to emit:
i) light of a first defined power into the first fiber core;
ii) light of a second defined power into the second fiber core; and
iii) light of a third defined power into the third fiber core;
c) a first light power detector optically connected to the first fiber core, a second light power detector optically connected to the second fiber core, and a third light power detector optically connected to the third fiber core; and
d) a controller operatively coupled to the first, second and third light power detectors,
e) wherein, with the at least one light source emitting:
i) the light of the first defined power into the first fiber core shining at the mirror;
ii) the light of the second defined power into the second fiber core shining at the mirror; and
iii) the light of the third defined power into the third fiber core shining at the mirror, and
f) wherein, in comparison to the guidewire with no axial or lateral forces imparted to the atraumatic head so that the atraumatic head is axially aligned with the core wire and the mirror is spaced a first distance from the distal face of the optical fiber and so that reflected percentages of light of the first, second and third defined powers are reflected by the mirror back to the distal face of the optical fiber with a first percentage of the reflected percentage of first defined light power captured by and traveling along the first fiber core to the first light power detector, a second percentage of the reflected percentage of second defined light power captured by and traveling along the second fiber core to the second light power detector, and a third percentage of the reflected percentage of third defined light power captured by and traveling along the third fiber core to the third light power detector, the first, second and third percentages of the reflected percentages of the first, second and third defined light power being determinable by the controller,
with only an axial force imparted to the atraumatic head of the guidewire to cause the atraumatic head to assume an orientation still axially aligned with the core wire but with the distal spring compressed sc that the mirror is spaced a second distance from the distal face of the optical fiber, the second distance being less than the first distance, a fourth percentage of the reflected percentage of the first defined light power is captured by and travels along the first fiber core to the first light power detector, a fifth percentage of the reflected percentage of the second defined light power is captured by and travels along the second fiber core to the second light power detector, and a sixth percentage of the reflected percentage of the third defined light power is captured by and travels along the third fiber core to the third light power detector, the respective differences between the first and fourth percentages of the reflected percentages of the first defined light power, the second and fifth percentages of the reflected percentages of the second defined light power, and the third and sixth percentages of the reflected percentages of the third defined light power being determinable by the controller to calculate the magnitude of the axial force imparted to the atraumatic head, and g) wherein, with both axial and lateral forces imparted to the atraumatic head of the guidewire, to cause the atraumatic head and the distal spring of the distal hypotube to deflect out of axial alignment with the core wire and with respect to the distal face of the optical fiber, the mirror is spaced a third distance from the first fiber core, a fourth distance from the second fiber core and a fifth distance from the third fiber core, the third, fourth and fifth distances being different than the first and second distances, so that in comparison to the first, second and third percentages of the reflected percentages of the first, second and third defined light powers, an axial and lateral force induced seventh percentage of the reflected percentage of the first defined light power is captured by and travels along the first fiber core to the first light power detector, an axial and lateral force induced eighth percentage of the reflected percentage of the second defined light power is captured by and travels along the second fiber core to the second light power detector, and an axial and lateral force induced ninth percentage of the reflected percentage of the third defined light power is captured by and travels along the third fiber core to the third light power detector, and wherein at least the difference between the first and seventh percentages of the reflected percentage of the first defined light power captured by and traveling along the first fiber core to the first light power detector is different than the differences between the second and eighth percentages of the reflected percentage of the second defined light power captured by and traveling along the second fiber core to the second light power detector and the third and ninth percentages of the reflected percentage of the third defined light power captured by and traveling along the third fiber core to the third light power detector, and wherein the controller is programmed to use the differences between the first and seventh percentages of the reflected first defined light power, the second and eighth percentages of the reflected second defined light power, and the third and ninth percentages of the reflected third defined light power to calculate a magnitude and vector of the axial and lateral forces imparted to the atraumatic head.

8. The guidewire assembly of claim 7, wherein the mirror is provided with a patterned reflectance that varies along a radius from a central area of reflectance.

9. The guidewire assembly of claim 8, wherein the patterned reflectance of the mirror comprises the central area of reflectance having a first light reflectance $R_1$ and at least one annular ring of reflectance having a second light reflectance $R_2$, and wherein $R_1$ is different than $R_2$, and wherein the first percentages of the first defined light power captured by and traveling along the first fiber core to the first light power detector, the second percentages of the second defined light power captured by and traveling along the second fiber core to the second light power detector and the third percentages of the third defined light power captured by and traveling along the third fiber core to the third light power detector from the first and second light reflectances $R_1$ and $R_2$ of the mirror with no axial or lateral forces imparted to the atraumatic head in comparison to the fourth percentages of the first defined light power captured by and traveling along the first fiber core to the first light power detector, the fifth percentages of the second defined light power captured by and traveling along the second fiber core to the second light power detector, and the sixth percentages of the third defined light power captured by and traveling along the third fiber core to the third light power detector from the first and second light reflectances $R_1$ and $R_2$ of the mirror with only an axial force imparted to the atraumatic head is determinable by the controller to calculate the magnitude of the axial force imparted to the atraumatic head, and wherein the seventh percentages of the first defined light power captured by and traveling along the first fiber core to the first light power detector, the eighth percentages of the second defined light power captured by and traveling along the second fiber core to the second light power detector, and the ninth percentages of the third defined light power captured by and traveling along the third fiber core to the third light power detector from the first and second light reflectances $R_1$ and $R_2$ of the mirror with both axial and lateral forces imparted to the atraumatic head in comparison to the respective first, second and third percentages of the reflected percentages of the first, second and third defined light powers from the first and second light reflectances $R_1$ and $R_2$ of the mirror with no axial or lateral forces imparted to the atraumatic head or, in comparison to the respective fourth, fifth and sixth percentages of the reflected percentages of the first, second and third defined light powers from the first and second light reflectances $R_1$ and $R_2$ of the mirror with only an axial force imparted to the atraumatic head is determinable by the controller to calculate the magnitude and vector of the axial and lateral forces imparted to the atraumatic head.

10. The guidewire assembly of claim 9, wherein the patterned reflectance of the mirror comprises the central area of reflectance having the first light reflectance $R_1$ and at least a first, a second and a third annular rings of reflectance having respective second, third and fourth light reflectances $R_2$, $R_3$ and $R_4$ at progressively greater first, second and third radial distances from the central area of reflectance, and wherein the light reflectances $R_1$, $R_2$, $R_3$ and $R_4$ are different from each other.

11. The guidewire assembly of claim 10, wherein the first light reflectance $R_1$ of the central area of reflectance of the mirror and the second, third and fourth light reflectances $R_2$, $R_3$ and $R_4$ of the respective first, second and third annular rings of reflectance are each divided into quadrants of reflectance, and wherein the quadrants of reflectance of each of the light reflectances $R_1$, $R_2$, $R_3$ and $R_4$ are different from each other.

12. The guidewire assembly of claim 10, wherein the first light reflectance $R_1$ of the central area of reflectance of the mirror and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

13. The guidewire assembly of claim 7, wherein the first, second and third fiber cores are evenly spaced at 120° intervals in the optical fiber.

14. The guidewire assembly of claim 7, wherein the at least one light source is selected from a Superluminescent Light Emitting Diode (SLED) and a scanning laser.

15. The guidewire assembly of claim 7, wherein the at least one light source comprises a first light source optically connected to the first fiber core, a second light source optically connected to the second fiber core, and a third light source optically connected to the third fiber core.

16. The guidewire assembly of claim 15, wherein the first, second and third light sources are narrow linewidth lasers.

17. The guidewire assembly of claim 7, wherein the distal spring of the distal hypotube comprises a coil spring or a slotted spring.

18. The guidewire assembly of claim 7, wherein a proximal coil spring is supported on the core wire.

19. The guidewire assembly of claim 7, wherein an optical connector optically connects the controller and an external optical fiber to the optical fiber of the guidewire.

20. The guidewire assembly of claim 19, wherein the optical connector has an electromechanical actuator, and wherein the controller is programmed to send a haptic vibration signal to the electromechanical actuator.

21. The guidewire assembly of claim 20, wherein the electromechanical actuator is selected from the group of a vibration motor, an eccentric rotating mass (ERM) actuator driven by an electronic circuit, a linear resonant actuator, and a piezoelectric actuator.

22. The guidewire assembly of claim 20, wherein the controller is programmed to vary at least one of a frequency and an amplitude of the haptic vibration signal to indicate the magnitude and vector of the axial and lateral forces imparted to the atraumatic head.

23. The guidewire assembly of claim 7, wherein the controller is further programmed to calculate an orientational value of the atraumatic head with respect to its axial alignment or non-alignment with the core wire from any one of:
   a) the first percentage of the reflected percentage of the first defined light power captured by and traveling along the first fiber core to the first light power detector, the second percentage of the reflected percentage of the second defined light power captured by and traveling along the second fiber core to the second light power detector, and the third percentage of the reflected percentage of the third defined light power captured by and traveling along the third fiber core to the third light power detector with no axial force imparted to the atraumatic head;
   b) the fourth percentage of the reflected percentage of the first defined light power captured by and traveling along the first fiber core to the first light power detector, the fifth percentage of the reflected percentage of the second defined light power captured by and traveling along the second fiber core to the second light power detector, and the sixth percentage of the reflected percentage of the third defined light power captured by and traveling along the third fiber core to the third light power detector with only the axial force imparted to the atraumatic head; and c) the seventh percentage of the reflected percentage of the first defined light power captured by and traveling along the first fiber core to the first light power detector, the eighth percentage of the reflected percentage of the second defined light power captured by and traveling along the second fiber core to the second light power detector, and the ninth percentage of the reflected percentage of the third defined light power captured by and traveling along the third fiber core to the third light power detector with both axial and lateral forces imparted to the atraumatic head.

24. A guidewire, comprising:

a) a core wire extending along a longitudinal axis from a core wire proximal end to a core wire distal portion having a core wire distal end, wherein a core wire lumen extends to the core wire proximal and distal ends;

b) a distal hypotube providing a hypotube lumen extending from a hypotube proximal portion to a hypotube distal portion, wherein the distal hypotube extends distally from the core wire distal end, and a distal spring is supported by the distal hypotube intermediate the hypotube proximal and distal portions;

c) an atraumatic head connected to the distal hypotube distal portion;

d) an optical fiber extending through the core wire lumen, wherein at least one fiber core extends through the optical fiber to a distal face of the optical fiber; and e) a mirror supported by the atraumatic head, wherein the mirror faces proximally but is spaced distally from the at least one fiber core at the distal face of the optical fiber, and wherein the mirror is provided with a patterned reflectance that varies along a radius from a central area of reflectance.

25. The guidewire of claim 24, wherein the patterned reflectance of the mirror comprises the central area of reflectance having a first light reflectance $R_1$ and at least one annular ring of reflectance having a second light reflectance $R_2$, and wherein $R_1$ is different than $R_2$.

26. The guidewire of claim 25, wherein the first light reflectance $R_1$ of the central area of reflectance of the mirror and the second, third and fourth light reflectances $R_2$, $R_3$ and $R_4$ of the respective first, second and third annular rings of reflectance are each divided into fractional segments of reflectance, and wherein the fractional segments of reflectance of each of the light reflectances $R_1$, $R_2$, $R_3$ and $R_4$ are different from each other.

27. The guidewire of claim 24, wherein a housing is supported by the core wire distal portion, the housing having a housing lumen that extends to a distal end of the housing, the housing lumen being in open communication with the core wire lumen, and wherein the optical fiber extends through the core wire and housing lumens to the housing distal end.

* * * * *

UNITED STATES PATENT AND TRADEMARK OFFICE
CERTIFICATE OF CORRECTION

| | |
|---|---|
| PATENT NO. | : 11,086,073 B2 |
| APPLICATION NO. | : 17/144447 |
| DATED | : August 10, 2021 |
| INVENTOR(S) | : John Michael Hayes and Jim Kelley |

It is certified that error appears in the above-identified patent and that said Letters Patent is hereby corrected as shown below:

In the Claims

Column 18, Line 32 (Claim 4, Line 2) delete "comp rises" and insert --comprises--

Column 19, Line 62 (Claim 7, Line 62) delete "sc" and insert --so--

Signed and Sealed this
Twenty-sixth Day of March, 2024

*Katherine Kelly Vidal*

Katherine Kelly Vidal
*Director of the United States Patent and Trademark Office*